(12) United States Patent
Bolduc et al.

(10) Patent No.: US 9,974,671 B2
(45) Date of Patent: May 22, 2018

(54) DEVICES AND METHODS FOR TREATING ANEURYSMS AND OTHER VASCULAR CONDITIONS

(71) Applicant: Medtronic Vascular, Inc., Santa Rosa, CA (US)

(72) Inventors: Lee Bolduc, Redwood City, CA (US); Bart Muhs, Guilford, CT (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 82 days.

(21) Appl. No.: 14/879,606

(22) Filed: Oct. 9, 2015

(65) Prior Publication Data

US 2016/0120667 A1    May 5, 2016

Related U.S. Application Data

(60) Provisional application No. 62/074,499, filed on Nov. 3, 2014.

(51) Int. Cl.
*A61F 2/07* (2013.01)
*A61F 2/89* (2013.01)
(Continued)

(52) U.S. Cl.
CPC ................ *A61F 2/856* (2013.01); *A61F 2/07* (2013.01); *A61F 2/848* (2013.01); *A61F 2/89* (2013.01);
(Continued)

(58) Field of Classification Search
CPC .................. A61F 2/07; A61F 2002/061; A61F 2002/075; A61F 2002/065; A61F 2/856; A61F 2/89; A61F 2/954; A61F 2230/0069; A61F 2002/828; A61F 2220/0016; A61F 2/86; A61F 2/06; A61F 2002/8483
See application file for complete search history.

(56) References Cited

U.S. PATENT DOCUMENTS 8,075,570 B2   12/2011   Bolduc
8,231,639 B2    7/2012   Bolduc
(Continued)

FOREIGN PATENT DOCUMENTS

EP        2591752        5/2013

OTHER PUBLICATIONS

Jan. 18, 2016, The International Search Report and the Written Opinion of the International Searching Authority, PCT/US2015-055198.

*Primary Examiner* — Ann Schillinger

(57) ABSTRACT

A fenestrated aortic cuff is configured to be delivered endovascularly to a target region, deployed, fastened, and sealed to a vessel wall, e.g., in a neck region of an aortic aneurysm. Example fenestrated cuffs provide a suitable landing zone for a commercially available endograft, which may be, in some cases, positioned below or above the renal arteries in order to complete exclusion of an abdominal aortic aneurysm (AAA) or a thoracic aortic aneurysm (TAA), respectively, from systematic circulation. In some cases, fenestrated cuff function is facilitated and improved by employing active fixation and sealing mechanisms, including, e.g., helical fasteners, which may allow deployment of the fenestrated cuff in short neck regions with limited sealing area.

5 Claims, 17 Drawing Sheets

(51) Int. Cl.
*A61F 2/856* (2013.01)
*A61F 2/848* (2013.01)
*A61F 2/06* (2013.01)

(52) U.S. Cl.
CPC ... *A61F 2002/061* (2013.01); *A61F 2002/072* (2013.01); *A61F 2002/075* (2013.01)

(56) References Cited

U.S. PATENT DOCUMENTS

| | | | |
|---|---|---|---|
| 2003/0199967 A1* | 10/2003 | Hartley | A61F 2/07 623/1.13 |
| 2010/0318174 A1 | 12/2010 | Shaolian et al. | |
| 2011/0087320 A1* | 4/2011 | Bolduc | A61B 17/064 623/1.35 |
| 2013/0116773 A1* | 5/2013 | Roeder | A61F 2/07 623/1.15 |

* cited by examiner

DEVICES AND METHODS FOR TREATING ANEURYSMS AND OTHER VASCULAR CONDITIONS

RELATED APPLICATIONS

This application claims the benefit of U.S. Provisional Application No. 62/074,499 filed on Nov. 3, 2014, entitled "DEVICES AND METHODS FOR TREATING ANEURYSMS AND OTHER VASCULAR CONDITIONS" of Lee Bolduc et al., which is incorporated herein by reference in its entirety.

BACKGROUND

The weakening of a vessel wall from damage or disease can lead to vessel dilatation and the formation of an aneurysm. Left untreated, an aneurysm can grow in size and may eventually rupture.

For example, aneurysms of the aorta occur in the abdominal region, usually in the infrarenal area between the renal arteries and the aortic bifurcation. Aneurysms can also occur in the tortuous thoracic region between the aortic arch and renal arteries. The rupture of an aortic aneurysm results in massive hemorrhaging and has a high rate of mortality.

Damage or disease of a vessel such as the aorta may also result in a dissection of the vessel wall. Aortic dissections are usually caused by a connective tissue disorder and/or high blood pressure. Left untreated, an aortic dissection can rupture or critically reduce blood flow to the heart, the brain, the spinal cord, the abdominal organs and the legs.

DETAILED DESCRIPTION

Figure 1A:
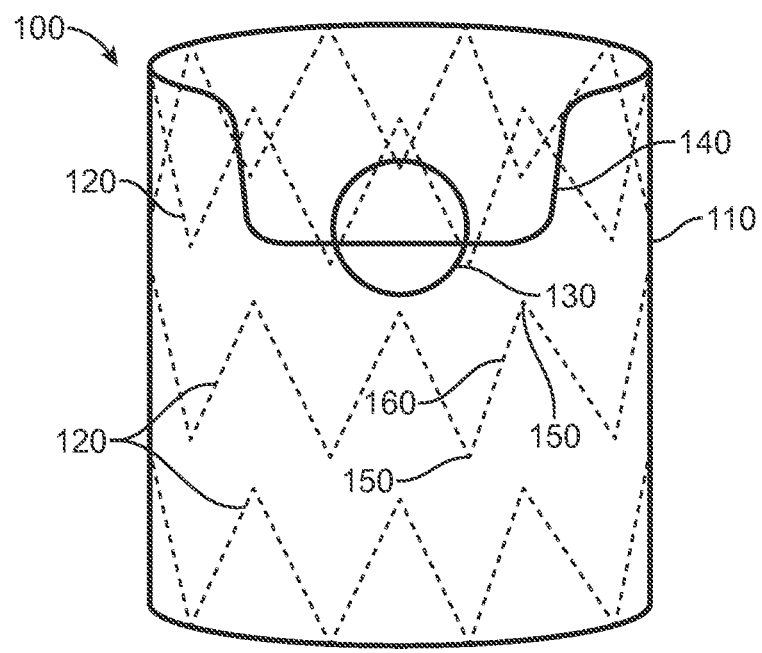
FIGS. 1A and 1B are perspective and elevation views, respectively, depicting an example fenestrated cuff.

Endovascular Aortic Aneurysm Repair (EVAR) is a procedure in which a stent-graft prosthesis (hereinafter endograft) is deployed endovascularly to treat an aneurysm, while leaving the aneurysm sac in place. EVAR may be favored over open surgical repair of aneurysms in order to, for example, shorten operation, intensive care, and total hospital times and lower postoperative morbidity. EVAR has become a viable alternative to open repair for a significant percentage of abdominal aortic aneurysm patients. In some cases, it is desirable to position the proximal end of the endograft as close to the orifice of the renal arteries as possible. In order to accomplish such positioning, endografts have been employed with a bare stent crossing the renal arteries to anchor the device in a suprarenal position. Additionally, aortic cuffs have been employed to proximally extend the main body of the endograft.

Some patients with aortic aneurysms present with what is sometimes referred to as a short proximal neck. The proximal neck refers to the healthy aortic tissue adjacent the aortic aneurysm sac in the infrarenal aorta. In abdominal aortic aneurysm (AAA) patients, the neck is proximal to the aneurysmal sac, between the aneurysm and the renal arteries. In thoracic aortic aneurysm (TAA) patients, there can be a proximal neck and a distal neck. Typically the proximal neck is between the aneurysm sac and the subclavian artery and the distal neck is between the aneurysm sac and the renal arteries. Currently, short proximal neck AAA and TAA patients are treated either through open procedure, off-label use of commercially available endografts or through the use of custom fenestrated endografts. Patients with short proximal and distal neck anatomy represent a significant challenge to proper treatment and exclusion of the AAA or TAA. At least one reason short proximal and distal neck anatomy patients present a significant challenge to efficacious treatment is the limited anatomical landing zone for the reparative endograft, which can equate to a limited seal and fixation zone for the endografts. Most commercially available endografts have a limitation on their neck length of 10 to 15 mm. If the neck is shorter than 10 mm, viable endograft options may be limited to custom fenestrated endografts. Such custom fenestrated endografts can take an extended time to produce and are expensive, require special training to correctly deploy and require extended procedure time to complete.

Examples according to this disclosure relate to a fenestrated aortic cuff to be delivered endovascularly to a target region, deployed, fastened, and sealed in a neck region of an aortic aneurysm. Example fenestrated cuffs provide a suitable landing zone for a commercially available endograft to be positioned below or above the renal arteries or below the subclavian artery in order to complete exclusion of an AAA or a TAA, respectively, from systematic circulation. It will be understood that although the following examples are described in the context of repair of aortic aneurysms, examples according to this disclosure may be employed for and applied to other types of vascular treatments, including, e.g., treatment of aneurysms in or localized dilation of other vessels.

Example prostheses can provide clinicians with a bridging endograft for commercially available endografts, including bifurcated grafts, in order to, e.g., complete the exclusion of an AAA or a TAA from systematic blood flow. Example prostheses can be deployed and sealed in relatively short aneurysmal necks, while maintaining satisfactory fixation and sealing performance. Example fenestrated prostheses are configured to work with and attach to commercially available AAA or TAA endografts.

Fenestrated cuffs in accordance with this disclosure can also be used as a repair for previously implanted endografts, which have exhibited migration and or endoleak. When endografts do not seal adequately at the proximal and/or distal landing zones, blood flow leaking back into the aneurysm sac is described as an endoleak. Endoleaks of this type would be considered a type 1 endoleak. The fenestrated cuff may be deployed inside of the migrated/leaking endograft to resolve a type 1 endoleak.

As noted, fenestrated cuffs in accordance with this disclosure are configured to provide a larger landing zone to deploy commercially available AAA or TAA endografts. In some cases, such cuff function is facilitated and improved by employing active fixation and sealing mechanisms, including helical fasteners in accordance with the following examples, which may allow deployment of the fenestrated cuff in short neck regions with limited sealing area. The combination of aortic cuff with helical fasteners, in accordance with examples of this disclosure, may also function to limit and/or prevent the aortic neck from dilating overtime, as the helical fasteners engage with the tissue and graft, which may slow or halt the progress of aneurysmal disease (dilation).

In an example, the fenestrated cuff will include a fenestration for a first vessel branching off the vessel in which the cuff is deployed and a scallop for a second branch vessel. In use to treat an aortic aneurysm, the fenestrated cuff can include a fenestration for the distal renal artery and a scallop for the superior renal artery. By utilizing the distal renal artery as a datum for locating and/or orienting the cuff in the aorta, the fenestrated aortic cuff may be able to accommodate a relatively larger number of patients with an off-the-shelf system. Currently, at least some custom fenestrated endografts use the superior mesenteric artery (SMA) as the datum and fenestrations in such endografts are aligned with both the inferior and superior renal arteries. In addition, only providing a fenestration for one renal artery and accommodating the opposite renal artery with a scallop may reduce the number of renal complications (acute and long term). Employing such a fenestrated cuff with active fixation mechanisms, e.g. helical fasteners, may also function to secure the position of the fenestration and scallop relative to the associated renal arteries.

Fenestrated cuffs in accordance with this disclosure can be fabricated in different proximal diameters and sized to the aortic neck to be treated. For example, the proximal diameter of the fenestrate cuff can be in a range from about 16 to about 46 millimeters (mm). In another example, the proximal diameter of the fenestrate cuff can be in a range from about 18 to about 42 mm. The overall length of the fenestrated cuff can be in a range from about 3 to about 8 centimeters (cm). In another example, the length of the cuff can be in a range from about 4 to about 6 cm.

Example fenestrated cuffs include a generally cylindrical graft through which the fenestration and scallop are disposed and one more stent structures. In one example, the cuff includes a cylindrical graft including a fenestration configured to be aligned with the distal renal artery and a scallop configured to be aligned with the superior renal artery. The cuff also includes a plurality of axially offset stent rings coupled to the graft, which are configured to allow the cuff to expand and contract. The stent rings are generally disposed circumferentially around the graft. In an example, one or more of the stent rings also extend axially. In the axial direction (e.g., in a direction generally parallel to the central axis of the graft and/or ring), one or more of the stent rings can include a triangle wave-form shape including adjacent apices connected to one another by linear (or curved) stent segments. Adjacent apices of the stent ring alternate in axial orientation from pointing toward the distal end of the cuff to pointing toward the proximal end of the cuff. Such example stent rings can expand and contract radially by being fabricated from a flexible, resilient material that allows the stent ring to bend at the apices. Example stent rings appropriate for use with fenestrated cuffs in accordance with this disclosure are described in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY," the entire contents of which is incorporated herein by reference.

The proximal stent of example fenestrated cuffs may function to provide sealing of the cuff to the vessel wall and prevent or inhibit enfolding of the graft material into the vessel lumen. Additionally, the distal stent may be used as a mechanism to couple the fenestrated graft to a commercially available endograft, including bifurcated grafts, in order to complete the exclusion of an aneurysm from systematic blood flow.

As noted, the fenestrated cuff can include stent rings disposed circumferentially around the graft, which also extend axially. The fenestrated cuff may include at least one distal stent ring sewn or otherwise attached to the graft material such that the stent ring is disposed within the lumen of the graft.

The proximal stent ring can also include external protrusions to increase the fixation of the cuff to the aorta. These can take the form of hooks and/or barbs and can be fabricated from the stent itself or added to the stent through a secondary manufacturing process. As an alternative or in addition to enfolding stents, the graft material may include loops of fabric, suture and/or different textures of fabric to better engage with retention features of the endograft (hooks and or barbs). In addition these features could help increase the sealing area by providing a gasket like effect. As noted, multiple, axially offset stent rings may be employed in fenestrated cuffs in accordance with this disclosure. Additionally, a single, continuous stent ring may be employed, which is arranged circumferentially around the cuff (inside or outside the graft) along a helical path such that the single stent ring wraps around the cuff between proximal and distal ends thereof.

Fenestrated cuffs in accordance with this disclosure can include radiopaque markers to assist in locating and fixating the cuffs. In one example, a fenestrated cuff includes radiopaque markers for positioning the cuff within the lumen of a vessel and for positioning the fenestration and scallop at the targeted branch arteries. For example, the fenestrated cuff can include one or more radiopaque marker for positioning the cuff within the aorta and for aligning the fenestration with the distal renal artery and aligning the scallop with the superior rental artery. In addition, example fenestrated cuffs can include radiopaque markers to guide placement of fixation mechanisms, e.g., helical fasteners and to properly position commercially available endografts relative to the cuffs. In addition, the delivery system can include radiopaque markers along the shaft and or jacket to help the user align the delivery system in the correct orientation within the aorta.

The stents of fenestrated cuffs in accordance with this disclosure can be self-expanding. For example, the stent structure, whatever the particular form, can be fabricated from a shape-memory material, which is configured to change shape based on some parameter like temperature. In one example, the stent structure is fabricated from a nickel-titanium (also referred to as nitinol) and is configured to expand from a contracted condition when released from the delivery system. In another example, the stent rings may be fabricated from a resilient material and configured to be biased toward a radially expanded state. In such examples, the fenestrated cuff and associated stent can be contracted and retained by a delivery system and then released when the cuff has been located within the target vessel. In some examples, fenestrated cuffs can include a balloon expandable (or some other separate expansion mechanism) stent.

The material from which the graft of example fenestrated cuffs are fabricated may have the ability to seal with all commercially available endografts and may also be suitable for coupling the cuff and endografts through the use of known fixation mechanisms, including, e.g., barbs, hooks, radial force. Additionally, in some examples, the fenestrated cuff can be coupled to the endografts and the vessel wall using separately deployed active fixation mechanisms, including, e.g., helical fasteners. Example materials for the graft of a fenestrated cuff include polyesters, ePTFE and other suitable biocompatible materials.

Figure 1B:
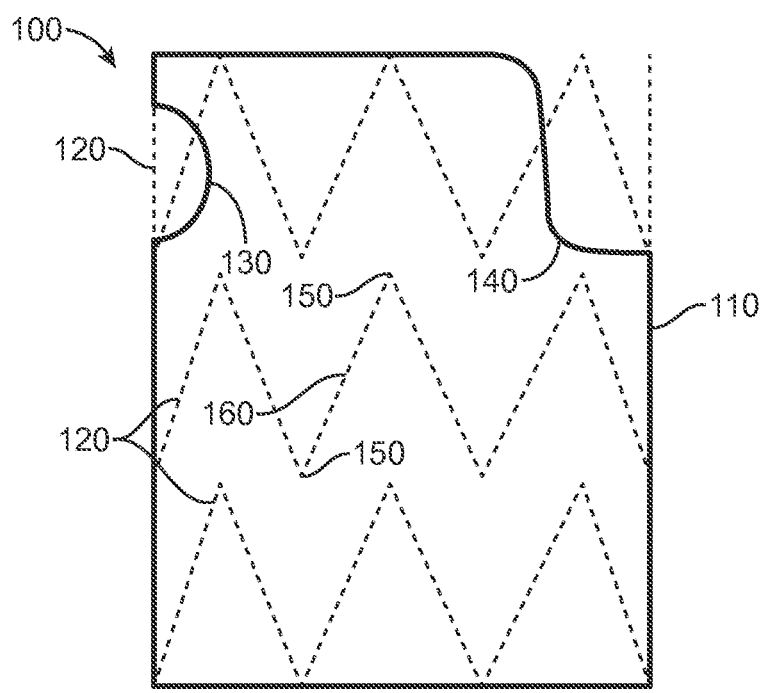

FIGS. 1A and 1B depict an example fenestrated cuff 100 including a generally cylindrical graft 110, stent rings 120, a fenestration 130, and a scallop 140. The entire fenestration 130 is shown in FIG. 1A for purposes of illustration although it is to be understood that only a portion of the fenestration 130 would be visible through the scallop 140 and the remaining portion would be blocked from visibility by the graft 110 in the view of FIG. 1A. The fenestration 130 and scallop 140 define openings in the graft 110. The fenestration 130 and scallop 140 are located such that when cuff 100 is positioned within, for example, the aorta, the fenestration 130 can be aligned with the orifice to the distal renal artery and the superior renal artery orifice is within the opening in the graft 110 defined by the scallop 140.

The material from which the graft 110 is fabricated may have the ability to seal with commercially available endografts and may also be suitable for coupling the cuff 100 and endograft through the use of one or more fixation mechanisms, including, e.g., barbs, hooks, radial force. Additionally, in some examples, the fenestrated cuff 100 can be coupled to an endograft and the wall of the vessel using separately deployed active fixation mechanisms, including, e.g., helical fasteners. Additionally, the fenestrated cuff 100 can be coupled to an endograft (e.g., independent of fixating to the wall of the vessel) using separately deployed active fixation mechanisms, including, e.g., helical fasteners. Example materials for the graft 110 include polyesters, ePTFE and other suitable biocompatible materials.

In FIGS. 1A and 1B, cuff 100 includes three axially offset stent rings 120. However, in other examples, fenestrated cuffs in accordance with this disclosure could include more or fewer stent rings, including, e.g., one, two or four or more. The stent rings 120 are generally disposed circumferentially around the graft 110 and extend axially. In the axial direction (e.g., in a direction generally parallel to the central axis of the graft 110 and/or stent rings 120), the stent rings 120 include a triangle wave-form shape including adjacent apices 150 connected to one another by linear stent segments 160. In some examples, the linear stent segments 160 connecting adjacent apices 150 of a stent ring 120 may all be the same length. However, in other examples, the linear stent segments 160 connecting adjacent apices 150 of a stent ring 120 may have different lengths (see the example of FIGS. 12A and 12B). The adjacent apices 150 of each stent ring 120 alternate in axial orientation from pointing toward the distal end of the cuff 100 to pointing toward the proximal end of the cuff 100. The stent rings 120 can be coupled to the graft 110 of cuff 100 in a variety of ways, including, e.g., by stitching the stent rings 120, or sandwiching the stent rings 120 between two layers of material, utilizing adhesives and/or thermal operations to bond the stent rings 120 to the graft 110.

Stent rings 120 can be configured to expand and contract. For example, the stent rings 120 can expand and contract radially by being fabricated from a flexible, resilient material that allows the stent ring 120 to bend at the apices 150. The stent rings 120 can be self-expanding. For example, the stent ring 120 can be fabricated from a shape-memory material, which is configured to change shape based on some parameter, e.g., temperature. In one example, the stent ring 120 is fabricated from a nickel-titanium (also referred to as nitinol) and is configured to expand from a contracted condition when released from the delivery system. In another example, the stent rings 120 may be fabricated from a resilient material and configured to be biased toward a radially expanded state. In such examples, the fenestrated cuff 100 and stent rings 120 can be contracted and retained by a delivery system and then released by a release mechanism of the delivery system when the cuff 100 has been located within the target region of the vessel. Examples of stent rings appropriate for use with fenestrated cuff 100 are described in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY," the entire contents of which is incorporated herein by reference.

In the example of FIGS. 1A and 1B, the distal apices 150 of the proximal stent ring 120 (the upper most stent ring 120 in FIGS. 1A and 1B) circumferentially spanning scallop 140, extend axially to and are coupled with graft 110. Coupling the proximal stent ring 120 to the graft 110 in this manner may function to provide stability to the proximal stent ring 120 and increase the sealing zone of the graft 110 to the wall of the vessel in which the cuff 100 is implanted.

The fenestration 130 and scallop 140 are arranged generally opposite one another on graft 110 of cuff 100. In one example, the fenestration 130 is generally circular. However, in some examples, fenestration 130 may be oval or elliptical shaped. In one example, the periphery of fenestration 130 is approximately 6 mm by 8 mm. The size of scallop 140 can be selected to accommodate different patient anatomies including different positions of the distal renal artery relative to the superior renal artery. In one example, the scallop 140 defines an opening in graft 110 that is approximately 10 mm in the axial direction and approximately 30 mm in the circumferential direction. In one example, the scallop 140 defines an opening in graft 110 that is from about 10 mm to about 20 mm in the axial direction and spans a range of angles circumferentially from about 20 degrees to about 70 degrees. In one example, scallop 140 defines an opening from about 12 mm to about 15 mm in the axial direction. In one example, scallop 140 defines an opening that spans a range of angles circumferentially from about 30 degrees to about 50 degrees.

Figure 2:
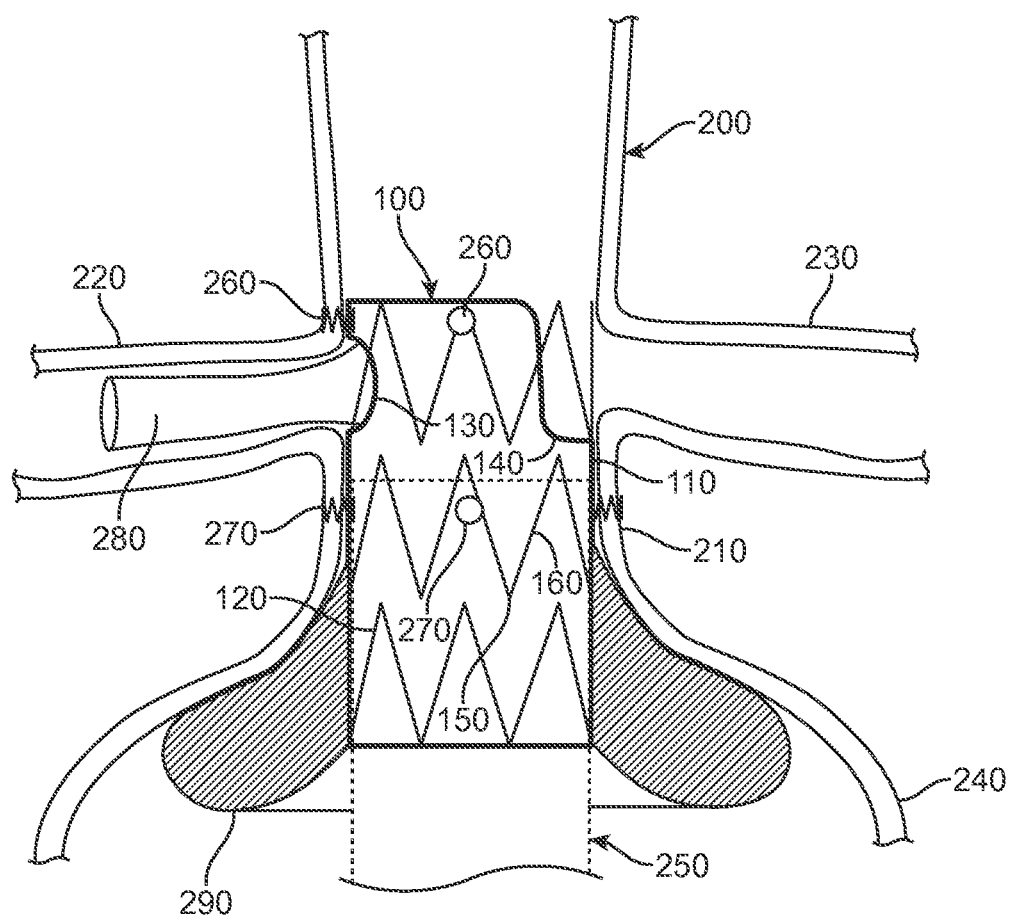
FIG. 2 depicts the example fenestrated cuff of FIGS. 1A and 1B implanted within the abdominal aorta.

FIG. 2 depicts example fenestrated cuff 100 implanted within abdominal aorta 200 to treat an AAA. Although fenestrated cuff 100 is described with reference to treatment of disease of the aorta, and, in particular, treatment of an AAA, cuff 100 and other fenestrated cuffs in accordance with this disclosure can be employed to treat the same or different conditions, in other locations, including, e.g., treating disease in the thoracic aorta like TAA.

In the example of FIG. 2, cuff 100 is implanted within the aorta 200, which has a relatively short proximal neck 210. The proximal neck 210 of aorta 200 can be, for example, less than 10 mm. The proximal end of cuff 100 is suprarenal, or, in other words, proximal to the distal renal artery 220 and the superior renal artery 230. The distal end of cuff 100 extends beyond the proximal neck 210 into the sac 240 of the aortic aneurysm. Fenestration 130 is aligned with distal renal artery 220 and scallop 140 is aligned with the superior renal artery 230.

The fenestrated cuff 100 is deployed within and coupled to aorta 200. A commercially available endograft 250 is connected to the cuff 100 to complete exclusion of the aneurysm sac 240 from systematic blood flow. Depending on the location of aneurysm sac 240, endograft 250 can include a single lumen, or, in other cases, can be a bifurcated endograft that splits into two lumens for branching blood flow at the aortic bifurcation into the iliac arteries.

Endograft 250 can be coupled to cuff 100 in a variety of ways including barbs, hooks, and/or a radially outward force of a stent of the endograft 250. Additionally and as described in more detail below, endografts 250 and cuff 100 can be coupled by one or more separately delivered and deployed fasteners, including, e.g., distal helical fasteners 270 illustrated in FIG. 2. Endograft 250 and cuff 100 can also be coupled, alone or in combination with other mechanisms, using stent rings 120 of cuff 100 and similar stent rings included in the endograft 250. In one example, the proximal stent ring 120 of cuff 100 includes external protrusions to increase the fixation of the cuff 100 to the aorta 200. Such protrusions can take the form of hooks and/or barbs and can be fabricated from the stent itself or added to the stent through a secondary manufacturing process. The graft 110 material may include loops of fabric, suture and/or different textures of fabric to better engage with retention features of the endograft (hooks and or barbs). In addition these features could help increase the sealing area by providing a gasket like affect. Stent rings 120 may be in the form of multiple, axially offset stent rings. In other examples, a single helical stent ring 120 may be employed. In such cases, the single stent ring 120 may be arranged circumferentially around graft 110 (inside or outside) along a helical path such that the single stent ring 120 wraps around the cuff 100 between proximal and distal ends thereof.

Figure 3:
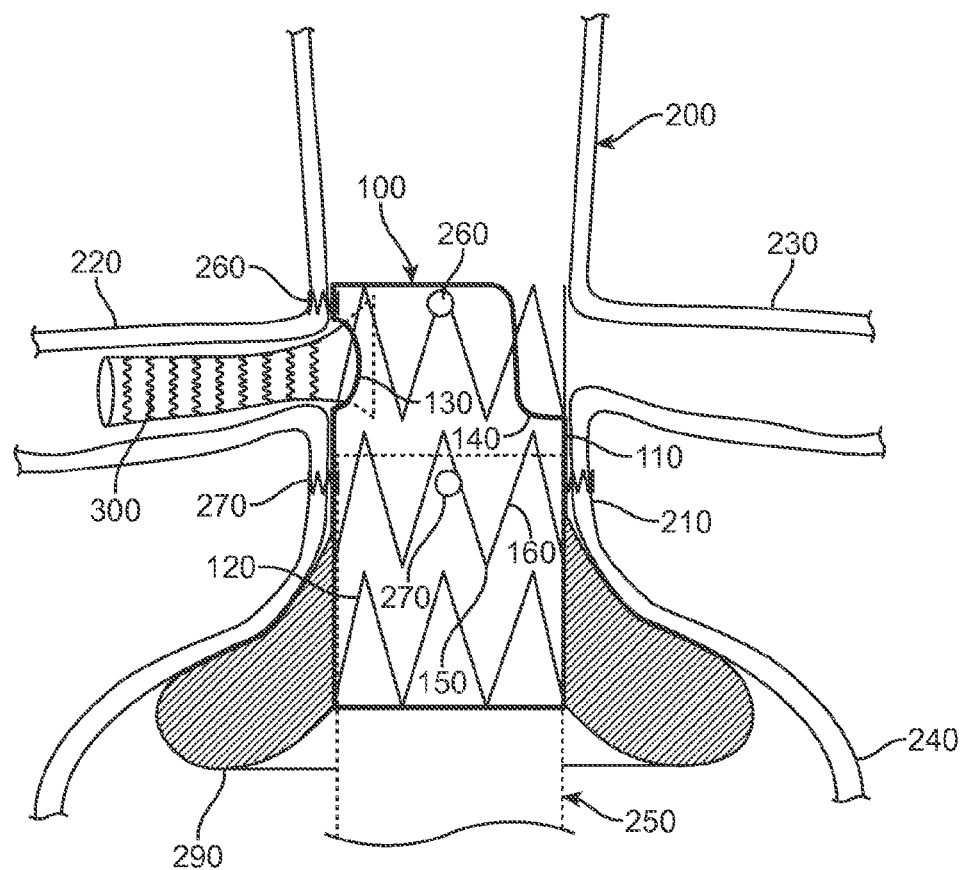
FIG. 3 depicts the fenestrated cuff of FIG. 1 with a covered renal stent.
Figure 4:
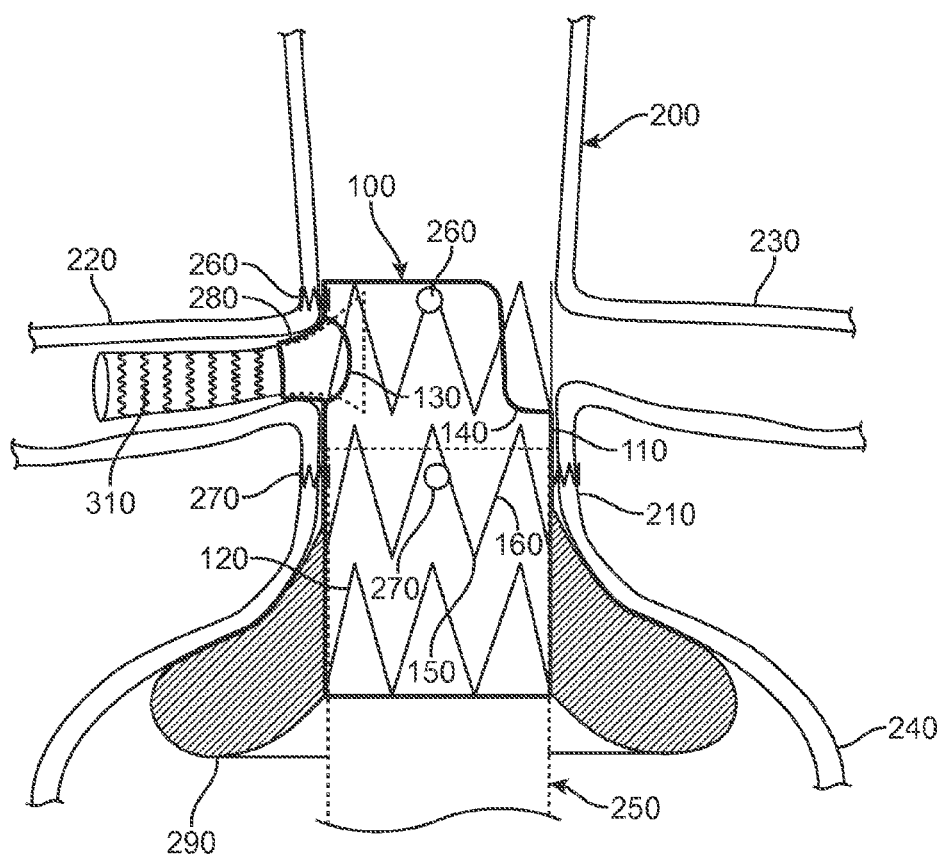
FIG. 4 depicts the fenestrated cuff of FIG. 1 with a fenestration graft and an uncovered renal stent.

The examples of FIGS. 2-4 illustrate endograft 250 delivered and deployed after cuff 100 and coupled telescopically within cuff 100. However, in other examples, fenestrated cuffs in accordance with this disclosure may also be delivered and deployed to repair an endograft that is already implanted. In such situations, the fenestrated cuff can be inserted within the lumen of the endograft and deployed such that the distal end of the cuff is arranged within the lumen of the endograft. After the cuff has been deployed and the stent of the cuff expanded into engagement with the implanted endograft and vessel wall, additional stabilizing and sealing measures can be taken. For example, an endovascular fastener applier in accordance with examples of this disclosure can be delivered to the site and one or more fasteners, e.g., helical fasteners, can be deployed to secure the cuff to the vessel and/or to couple the cuff and the endograft to one another. Such fasteners can also be used to repair damage or leaks in the previously implanted endograft.

In some cases, employing example fenestrated cuffs in this manner may serve to repair an endograft implanted in a short neck aneurysmal aorta, which endograft has migrated and/or developed endoleaks. In such a case, the fenestrated cuff may be employed to bridge the endograft to the short neck of the aneurysm to stabilize the endograft within the aorta and also to repair existing endoleaks. The fenestrated cuff and/or the separately delivered and deployed fasteners, e.g., helical fasteners can function to stabilize the endograft within the aorta and also to repair existing endoleaks.

Referring again to the example of FIG. 2, a number of mechanisms are included to assist in stabilizing the position of the cuff 100 within and sealing the cuff 100 to the wall of aorta 200. The stent rings 120 are configured to expand into engagement with and stabilize the location of cuff 100. Additionally, the stent rings 120 and graft 110 can facilitate tissue growth into cuff 100 to facilitate maintaining the position of the cuff 100 within aorta 200. Although not shown, additional mechanisms may be included in cuff 100 (e.g., not separately delivered and deployed) to stabilize the position of the cuff 100 within the aorta 200 and to couple the cuff 100 to the wall of the aorta 200, including, e.g., barbs and hooks.

Also stabilizing the position of and assisting to seal the cuff 100 to the wall of aorta 200 are proximal helical fasteners 260 and distal helical fasteners 270. Proximal fasteners 260 are infrarenal and distal helical fasteners 270 are implanted in the proximal neck of the aortic aneurysm. Both the proximal and the distal fasteners 260, 270 are distributed circumferentially around cuff 100 and penetrate the cuff 100 and the wall of aorta 200. Additionally, distal fasteners 270 are employed to at least augment the connection between cuff 100 and endograft 250. Proximal fasteners 260 include posterior and anterior fasteners and additional fastener(s) below and/or above the distal renal artery 220 at approximately 90 degrees to the posterior and anterior fasteners (to the left in the view shown in FIG. 2). Distal fasteners 270 include a posterior and an anterior fastener and two additional fasteners below the distal renal artery 220 at approximately 90 degrees to the posterior and anterior fasteners (to the left in the view shown in FIG. 2) and below the superior renal artery 230 at approximately 90 degrees to the posterior and anterior fasteners (to the right in the view shown in FIG. 2). In the example of FIG. 2, two sets of circumferentially disposed helical fasteners 260 and 270 are employed to secure and seal cuff 100 and endograft 250. However, in other examples, different numbers, arrangements, and types of separately delivered and deployed fasteners may be used in combination with fenestrated cuffs in accordance with this disclosure.

The example of FIG. 2 also includes fenestration graft or sleeve 280 defining a grafted lumen into distal renal artery 220 from the lumen of the graft 110 of cuff 100. Fenestration graft 280 includes an annular, and, in this example, generally cylindrical sleeve that extends from fenestration 130 into distal renal artery 220. Although not shown in FIG. 2, fenestration graft 280 may also include a stent structure to reinforce the graft and/or to facilitate inserting the fenestration graft 280 into the renal artery 220. Fenestration graft 280 may function to increase the surface area of cuff 100 for sealing the cuff 100 to the vascular wall(s) (e.g., aorta 200 and distal renal artery 220), which, in turn, may reduce the potential for endoleaks of the cuff 100.

The fenestration graft 280 may also allow uncovered renal stents to be used for the fenestration instead of covered renal stents. Additionally, the fenestration graft 280 may act as a buffer between the wall of distal renal artery 220 and such renal stent to reduce trauma to the vessel during implantation FIG. 3 illustrates fenestrated cuff 100 implanted and employed in conjunction with a covered renal stent 300. The covered renal stent 300 extends into and through the fenestration 130 of cuff 100 and is flared radially outward adjacent this junction. FIG. 3 illustrates the seal between the fenestration 130 and the outer diameter (OD) of the covered stent 300 in this example.

FIG. 4 illustrates fenestrated cuff 100 including fenestration graft/sleeve 280 coupled to and extending from fenestration 130. In this example, fenestrated cuff 100 and fenestration graft 280 are employed in combination with an uncovered stent 310. As illustrated, in the example of FIG. 4, a seal is provided along the length of the uncovered stent 310 and fenestration graft 280 in a region of overlap between the two structures.

Fenestration graft 280 can be sized and shaped to accommodate different patient anatomies. In one example, fenestration graft 280 is from about 1 mm to about 20 mm long. In another example, fenestration graft 280 is from about 1 mm to about 5 mm long. In one example, the diameter of fenestration graft 280 is from about 4 mm to about 10 mm. In another example, the diameter of fenestration graft 280 is from about 5 mm to about 8 mm.

The example of FIG. 2 includes expandable cavity 290, which may function to provide additional sealing of cuff 100 within aorta 200 to reduce the potential for blood flow leakage into the aneurysm sac 240. As illustrated in FIG. 2, expandable cavity 290 can be connected around the outer surface of the distal end of cuff 100 such that the cavity 290 can be expanded to fill the space between the cuff 100 and the distal portion of proximal neck 210 and the proximal portion of the aneurysm sac 240. When deployed and expanded, cavity 290 can include a toroid shape, surrounding the distal end of cuff 100. Expandable cavity 290 can be coupled to cuff 100 and collapsed before and during delivery of the cuff 100 to the target site within aorta 200, after which the cavity 290 can be expanded as shown in FIG. 2. In one example, the expandable cavity 290 can be filled with a settable polymer. In another example, the expandable cavity 290 can be filled with saline.

In one example, expandable cavity 290 may be two layers of material, which can be filled and/or expanded. For example, the area within the two layers of material may filled with an expandable polymer or other material to take on a predetermined shape or could simply fill a space to facilitate sealing the cuff 100 to the aorta 200.

Figure 5:
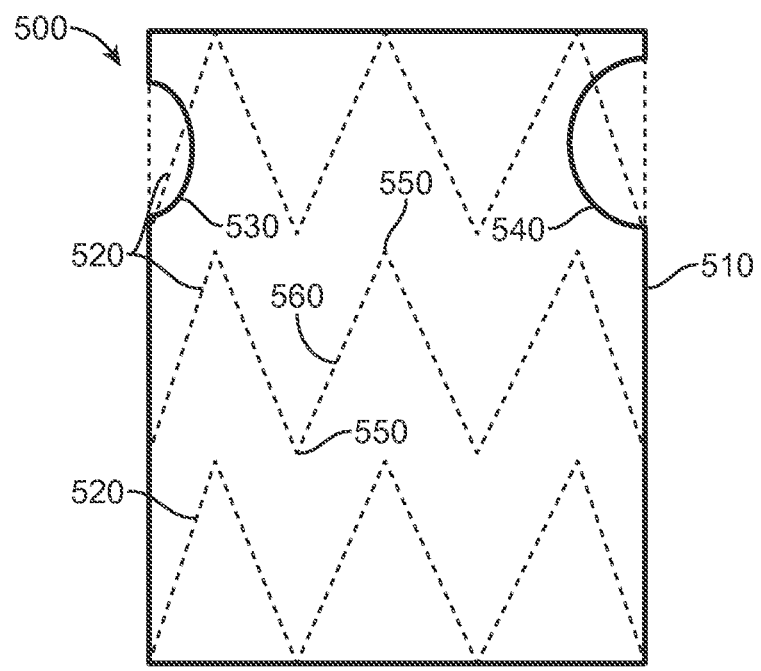
FIG. 5 is an elevation view depicting an alternative example fenestrated cuff in accordance with this disclosure.

Although the foregoing examples describe an example fenestrated cuff including a fenestration and a scallop, other fenestrated cuffs are also possible. FIG. 5 depicts an alternative example fenestrated cuff 500 in accordance with this disclosure. The fenestrated cuff 500 includes a generally cylindrical graft 510, stent rings 520, a first fenestration 530, and a second fenestration 540. The first and second fenestrations 530 and 540 define openings in the graft 510 and are located such that when cuff 500 is positioned within, for example, the aorta, the first fenestration 530 can be aligned with the orifice to the distal renal artery and the superior renal artery orifice is within the opening in the graft 510 defined by the second fenestration 540. As illustrated in this example, first and second fenestrations 530 and 540, respectively, may be different sizes, e.g., the second fenestration 540 may be larger than the first fenestration 530.

The first fenestration 530 and the second fenestration 540 are arranged generally opposite one another on graft 510 of cuff 500. In one example, the first and second fenestrations 530 and 540 are generally circular. However, in some examples, one or both of the first and second fenestrations 530 and 540 may be oval or elliptical shaped. The sizes and shapes of the first and second fenestrations 530 and 540 can be selected to accommodate different patient anatomies including different positions of the distal renal artery relative to the superior renal artery.

The structure, materials, functions, and features of the graft 510 and the stent rings 520 (including adjacent apices 550 connected by stent segments 560) of the fenestrated cuff 500 may be substantially similar those described above with reference to the graft 110 and the stent rings 120 of fenestrated cuff 100.

Figure 6:
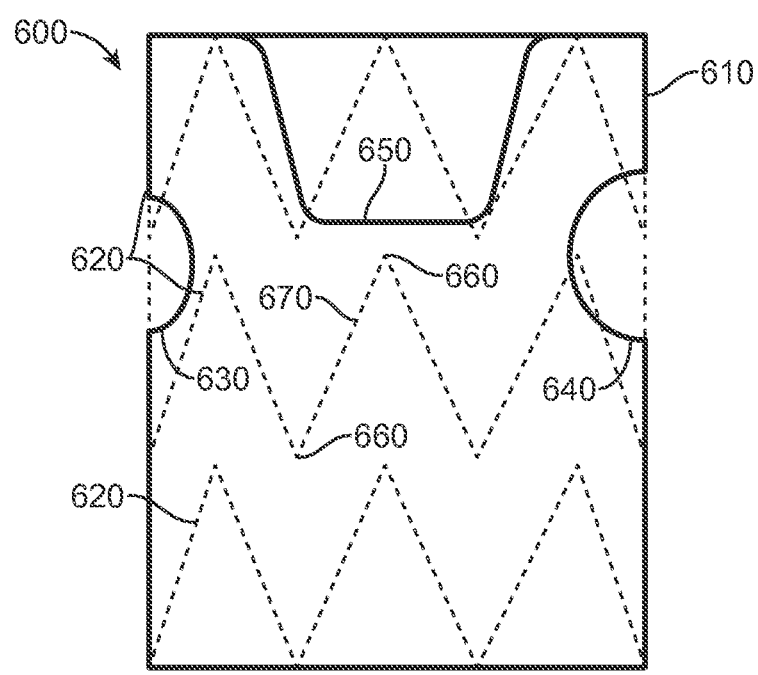
FIG. 6 is an elevation view depicting another example fenestrated cuff in accordance with this disclosure.

FIG. 6 depicts an alternative example fenestrated cuff 600 in accordance with this disclosure. The fenestrated cuff 600 includes a generally cylindrical graft 610, stent rings 620, a first fenestration 630, a second fenestration 640, and a scallop 650. The first and second fenestrations 630 and 640, respectively, and the scallop 650 define openings in the graft 610. The first and second fenestrations 630 and 640 are located such that when cuff 600 is positioned within, for example, the aorta, the first fenestration 630 can be aligned with the orifice to the distal renal artery and the superior renal artery orifice is within the opening in the graft 610 defined by the second fenestration 640. As illustrated in this example, first and second fenestrations 630 and 640, respectively, may be different sizes, e.g., the second fenestration 640 may be larger than the first fenestration 630.

The scallop 650 is arranged on the circumference of the graft 610 between the first and second fenestrations 630 and 640. The scallop 650 can be positioned relative to the first and second fenestrations 630 and 640 and sized such that when cuff 600 is positioned within, for example, the aorta, the superior mesenteric artery (SMA) is within the opening in the graft 610 defined by the scallop 650.

The first fenestration 630 and the second fenestration 640 are arranged generally opposite one another on graft 610 of cuff 600. In one example, the first and second fenestrations 630 and 640 are generally circular. However, in some examples, one or both of the first and second fenestrations 630 and 640 may be oval or elliptical shaped. The sizes and shapes of the first and second fenestrations 630 and 640 can be selected to accommodate different patient anatomies including different positions of the distal renal artery relative to the superior renal artery.

The structure, materials, functions, and features of the graft 610 and the stent rings 620 (including adjacent apices 660 connected by stent segments 670) of the fenestrated cuff 600 may be substantially similar those described above with reference to the graft 110 and the stent rings 120 of fenestrated cuff 100.

Figure 7:
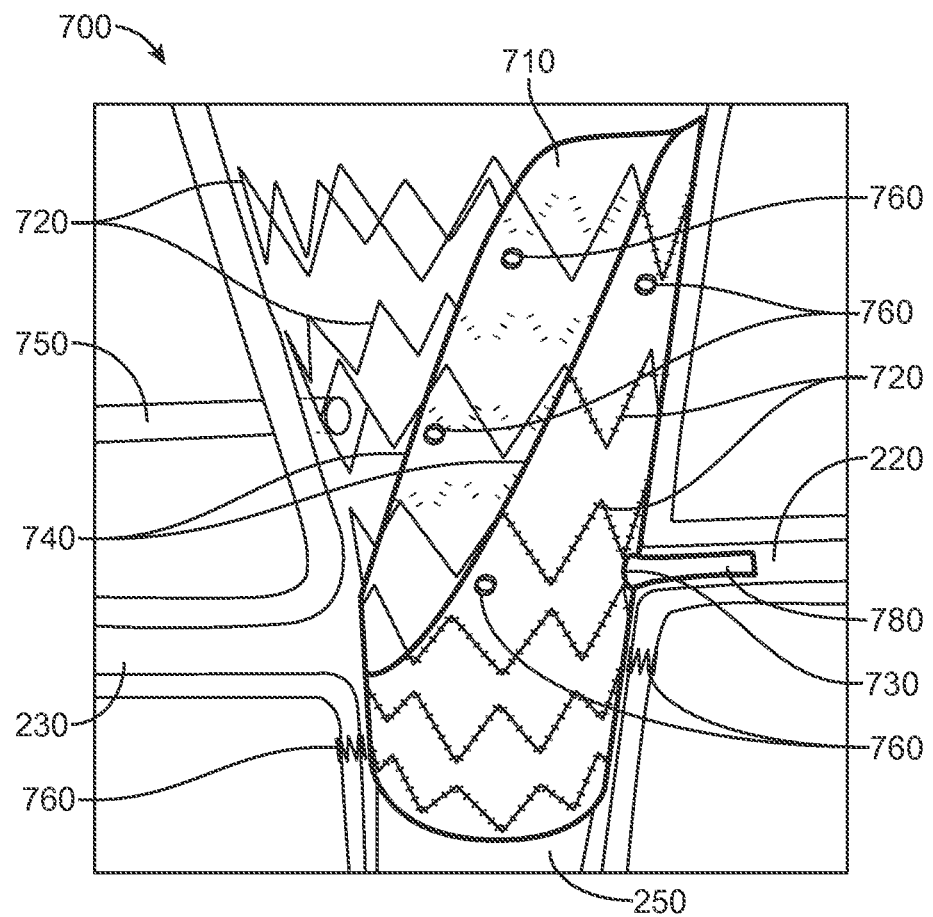
FIG. 7 is a perspective view depicting another example fenestrated cuff in accordance with this disclosure.

FIG. 7 depicts an alternative example fenestrated cuff 700 in accordance with this disclosure. The fenestrated cuff 700 includes a generally cylindrical graft 710, stent rings 720, a fenestration 730, and a beveled edge 740. The example of FIG. 7 also includes a fenestration graft 780 extending from fenestration 730 into distal renal artery 220. The fenestration 730 and the beveled edge 740 define openings in the graft 710. The example fenestrated cuff 700 is longer than some other example cuffs described above, including six stent rings 720 and graft 710 that extends proximally further up the aorta from the distal and superior renal arteries 220 and 230.

In some open surgical repairs of a diseased vessel like an aneurysmal aorta, the physician may cut the graft material with a large beveled edge, which is sometimes referred to as a Coral patch. The example fenestrated cuff 700 includes such a beveled edge 740 on the proximal end of the cuff. The beveled edge 740 may be defined by a planar cut in the graft 710 in a plane that is angled relative to the longitudinal axis of the cuff 700. The increased length and increased surface area of the cuff 700 may function to improve sealing the cuff 700 within a vessel, e.g., within the aorta. Additionally, the beveled edge 740 may define an opening in the graft 700 to accommodate multiple branch vessels, including, e.g., the superior renal artery 230 and the SMA 750. In one example, the beveled edge 740 is at approximately 60 degrees to the axis of the cuff 700 and is from about 2 to about 2.5 (cm) long (e.g., from the proximal end of the cuff 700 to the distal end of the beveled edge 740).

The fenestration 730 is located such that when cuff 700 is positioned within, for example, the aorta, the fenestration 730 can be aligned with the orifice to the distal renal artery 220. In one example, the fenestration 730 is generally circular. However, in some examples, the fenestration 730 may be oval or elliptical shaped. The size and shape of the fenestration 730 can be selected to accommodate different patient anatomies including different positions of the distal renal artery relative to the superior renal artery.

The beveled edge 740 is arranged on the circumference of the graft 710 generally opposite to the fenestration 730. The beveled edge 740 can be positioned relative to the fenestration 730 and sized such that when cuff 700 is positioned within, for example, the aorta, the superior renal artery 230 and the SMA 750 are within the opening in the graft 710 defined by the beveled edge 740.

The example of FIG. 7 also includes a plurality of helical fasteners 760 to stabilize the location of the cuff 700 and facilitate sealing the cuff 700 to the aorta (or other vessel within which the cuff is implanted). In this example, the helical fasteners 760 are arranged infrarenally, including along beveled edge 740. Additionally, a number of helical fasteners 760 are arranged in the proximal neck region.

Figure 8A:
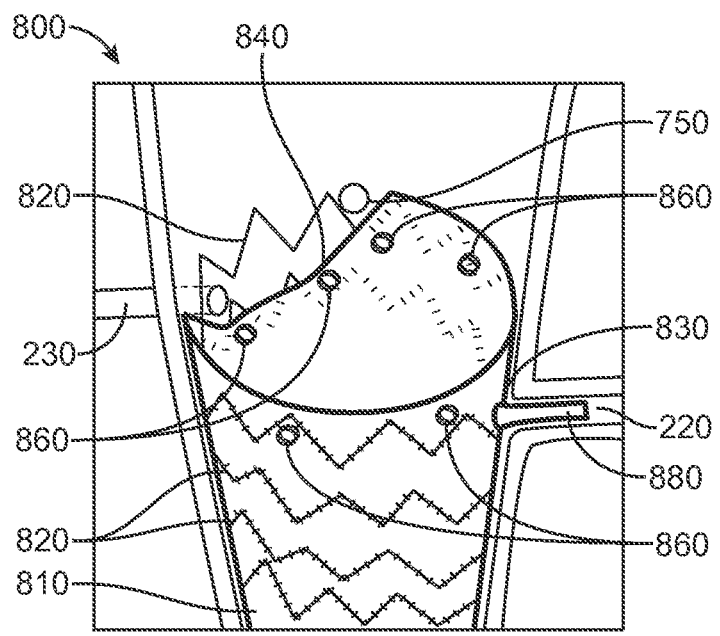
FIGS. 8A and 8B are perspective views depicting another example fenestrated cuff in accordance with this disclosure.
Figure 8B:
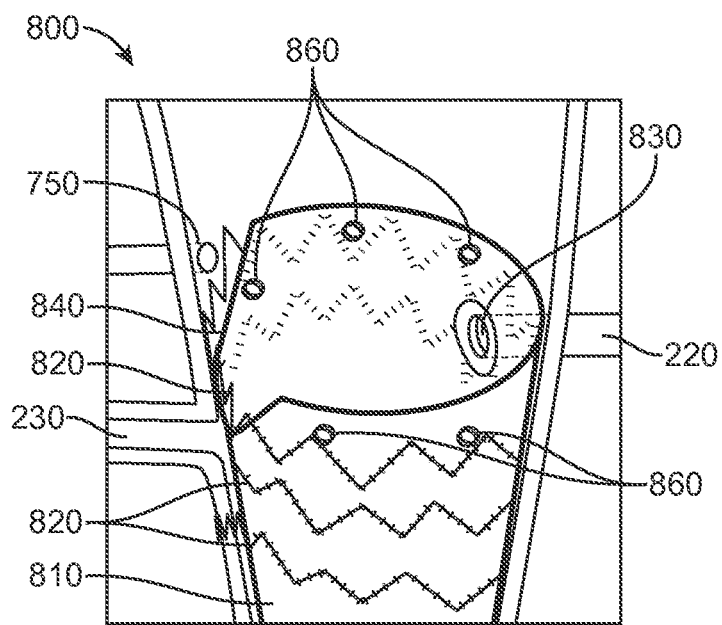

FIGS. 8A and 8B depict another example fenestrated cuff 800 including a generally cylindrical graft 810, stent rings 820, a fenestration 830, and a scallop 840. The example of FIGS. 8A and 8B also includes a fenestration graft 880 extending from fenestration 830 into distal renal artery 220. Fenestrated cuff 800 may be similar in size, shape, components, and/or function as fenestrated cuff 100. However, in this example, the portion of the proximal stent ring 820 spanning the scallop 840 is not connected to the graft 810 of the cuff 800. To assist with stabilization and sealing, however, a number of helical fasteners 860 are deployed along the periphery of the scallop 840.

Fenestrated cuffs in accordance with this disclosure can be delivered and deployed endovascularly using a variety of delivery systems/devices. In practice, the fenestrated cuff can be delivered and deployed prior to delivering a commercially available endograft and coupling the endograft to the cuff. In other cases, the fenestrated cuff can be delivered to repair an endograft already implanted within a vessel.

In one example, the fenestrated cuff delivery system includes multiple cuff retention mechanisms and multiple associated release mechanisms. For example, the cuff delivery system may include a delivery catheter in which the cuff is arranged and which includes one or more retention mechanisms for connecting the proximal end of the cuff to the delivery catheter and at least one retention mechanism for connecting the distal end of the cuff to the catheter. Such deployment features of the cuff delivery system may allow the cuff to be partially deployed, recovered, and fully deployed to aid in the positioning of the cuff within the aortic lumen (or another location) and positioning the fenestration(s) at the targeted renal artery (or other branch vessel). In addition, the delivery system may allow the cuff to be fully deployed but not released from the delivery system until the fenestration is completed with the placement of a renal graft/stent and additional fixation mechanisms, e.g., helical fasteners have been deployed.

In one example, the distal end of the delivery catheter includes a central shaft around which the cuff is arranged and which functions as a carrier for the cuff, multiple proximal and/or distal retaining means, a catheter tip component, and a retractable sleeve surrounding the cuff and central shaft. The sleeve surrounding the cuff is configured to be retracted to expose the cuff within the target region of a vessel. The proximal retaining means can include first and second proximal retaining means. The first proximal retaining means which can be attached and multiple areas of the cuff can function to retain at least a portion of the cuff in a radially compressed, and/or partially radially expanded condition prior to deployment. The second proximal retaining means can function to stabilize the cuff by inhibiting or preventing longitudinal and rotational movement of the cuff relative to the delivery catheter. Each of the first and second proximal retaining means also include independent or co-acting releasing means for releasing the first and second proximal retaining means and thereby partially or completely releasing the cuff from the delivery catheter. The distal retaining means can function to partially or completely retain the distal end of the cuff in a compressed or partially expanded state and connect the distal end of the cuff to the catheter. The proximal and distal retaining means can include a releasing means for activating/releasing the distal retaining means. Example releasing means may include a wide variety of devices, such as wire or wires, sutures, magnetics, or fluids, and may include sliding, pulling or pushing, for example. The releasing means may be operatively connected to/incorporated in and actuated from a handle connected to the proximal end of the delivery catheter. Additional details and examples of delivery systems appropriate for use with example fenestrated cuffs in accordance with this disclosure are described in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY."

Figure 9:
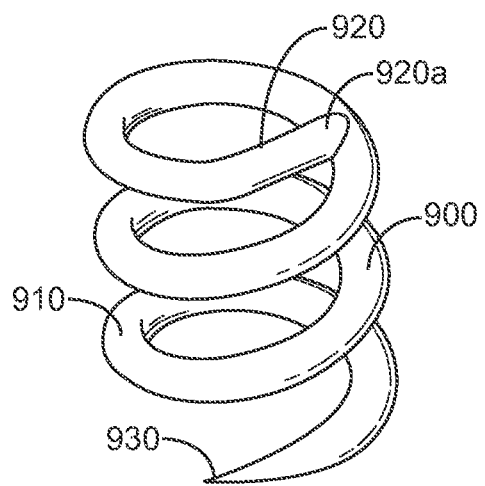
FIG. 9 is a perspective view of an example helical fastener.

FIG. 9 depicts an example helical fastener 900 in accordance with this disclosure and appropriate for use in conjunction with fenestrated cuffs. The helical fastener 900 includes a helical main body 910 including a plurality of coils. Fastener 900 also includes a proximal cross-bar 920 and a sharp distal tip 930 at either end of helical main body 910. The cross-bar 920 spans the diameter of fastener 900 and may be, in some examples, coupled to the main body 910 (e.g., by welding or some other coupling means).

Fastener 900 may be sized and configured to attach a prosthesis to a vessel wall and/or to attach two or more prostheses to one another. For example, fastener 900 may be sized and configured to attach a fenestrated cuff to the wall of the aorta and/or to attach the cuff to a commercially available endograft. As noted above, fastener 900 includes a helical main body 910. The helical main body 910 and sharp distal tip 930 allow the fastener 900 to pierce and engage tissue in response to rotation of main body 910, thereby securing attachment of, e.g., a fenestrated cuff to a vessel wall.

In one example, fastener 900 is manufactured from medical grade wire having a diameter between about 0.1 mm and 1.0 mm. In one example, fastener 900 is approximately between about 2 mm and 12 mm in over-all length and approximately between about 1.0 mm and 10 mm in maximum diameter. Distal tip 930 of main body 910 can be sharpened to facilitate atraumatic deployment through graft materials and vessel walls. Proximal end, including, cross-bar 920 of main body 910 can be closed to prevent over-penetration of fastener 900. In some examples, cross-bar 920 extends across the entire inner diameter of the proximal most coil of helical main body 910 and the extending end 920a of cross-bar 920 is connected to main body 910 such that the proximal end of fastener 900 does not have a terminating end, but, instead reconnects with itself. In one example, extending end 920a of cross-bar 920 is welded to main body 910. Structurally connecting cross-bar 920 to main body 910 in this or another similar manner can provide the strength necessary for fastener 900 to withstand the torque applied by fastener applicator driver to implant fastener 900 through a prosthesis and partially or completely through a vessel wall.

Example separately delivered and deployed fasteners used in combination with fenestrated cuffs in accordance with this disclosure can be implanted using a variety of different fastener delivery systems. In one example, helical fasteners are delivered and deployed using a fastener delivery shaft with a fastener driver at the distal end of the shaft. The delivery shaft can be delivered to the target region of a vessel through the lumen of a steerable, e.g., deflectable distal end, guide catheter. The fastener delivery shaft may be connected at the proximal end to a handle for manually rotating and deploying the helical fasteners or to a handle including controls and a rotational drive mechanism for mechanically or electromechanically deploying the helical fasteners. The driver at the distal end of the delivery shaft is connected to the handle and, in some cases, to a drive mechanism such that rotation of the handle or actuation of the drive mechanism causes the driver to rotate. The driver is configured to hold and deploy the helical fastener 900 by imparting the rotational force from the handle or drive mechanism onto the fastener 900, which, in turn, causes the fastener 900 to penetrate and rotate into cuff and tissue.

Additional details and examples of fastener delivery and deployment systems appropriate for use with example fenestrated cuffs in accordance with this disclosure are described in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY." Additional examples of fasteners and fastener applicator systems appropriate for use with example fenestrated cuffs in accordance with this disclosure are also described in U.S. Pat. No. 8,075,570, filed Nov. 29, 2002, and entitled "INTRALUMINAL PROSTHESIS ATTACHMENT SYSTEMS AND METHODS," and in U.S. Pat. No. 8,231,639, filed Feb. 25, 2004, and entitled "SYSTEMS AND METHODS FOR ATTACHING A PROSTHESIS WITHIN A BODY LUMEN OR HOLLOW ORGAN," the entire contents of each of which is incorporated herein by reference.

Figure 10A:
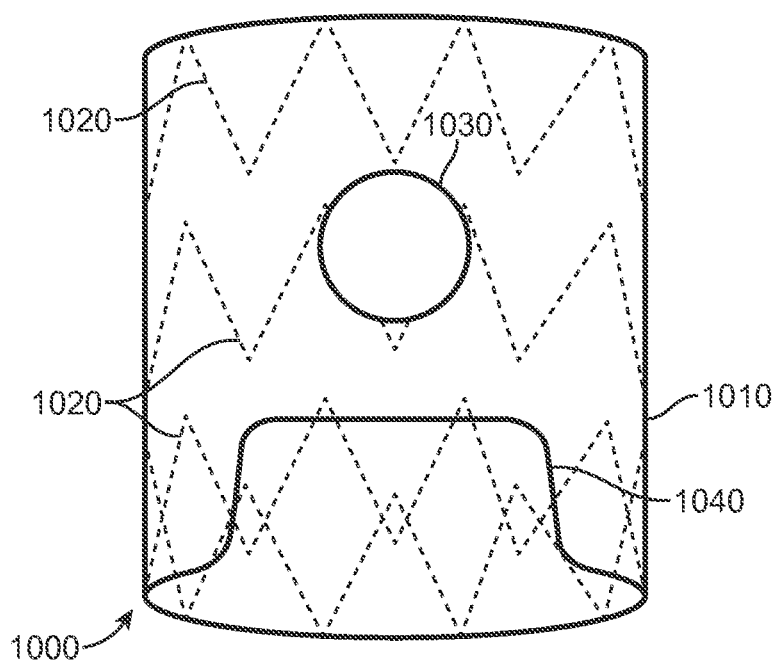
FIGS. 10A, 10B, and 10C depict another example fenestrated cuff in accordance with this disclosure for implantation within the thoracic aorta.
Figure 10B:
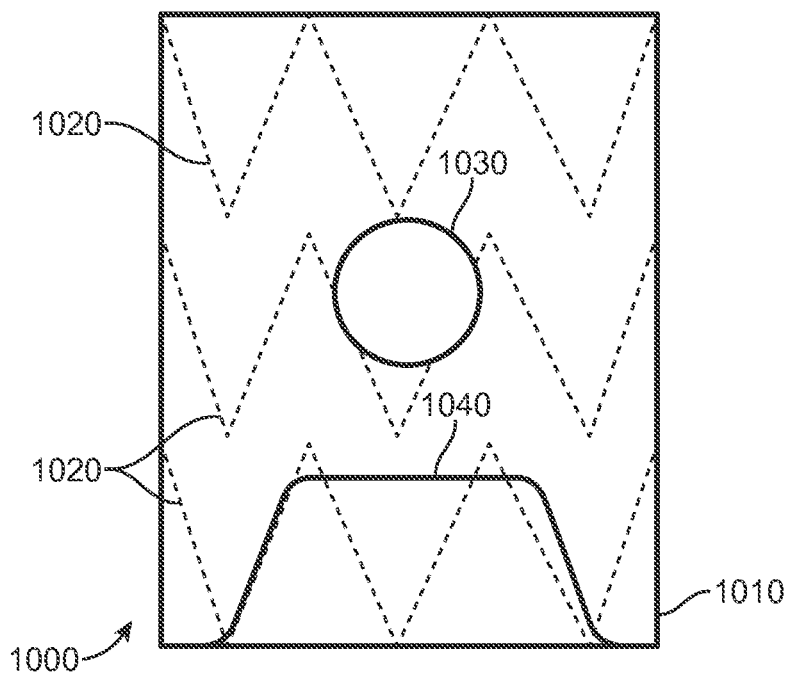
Figure 10C:
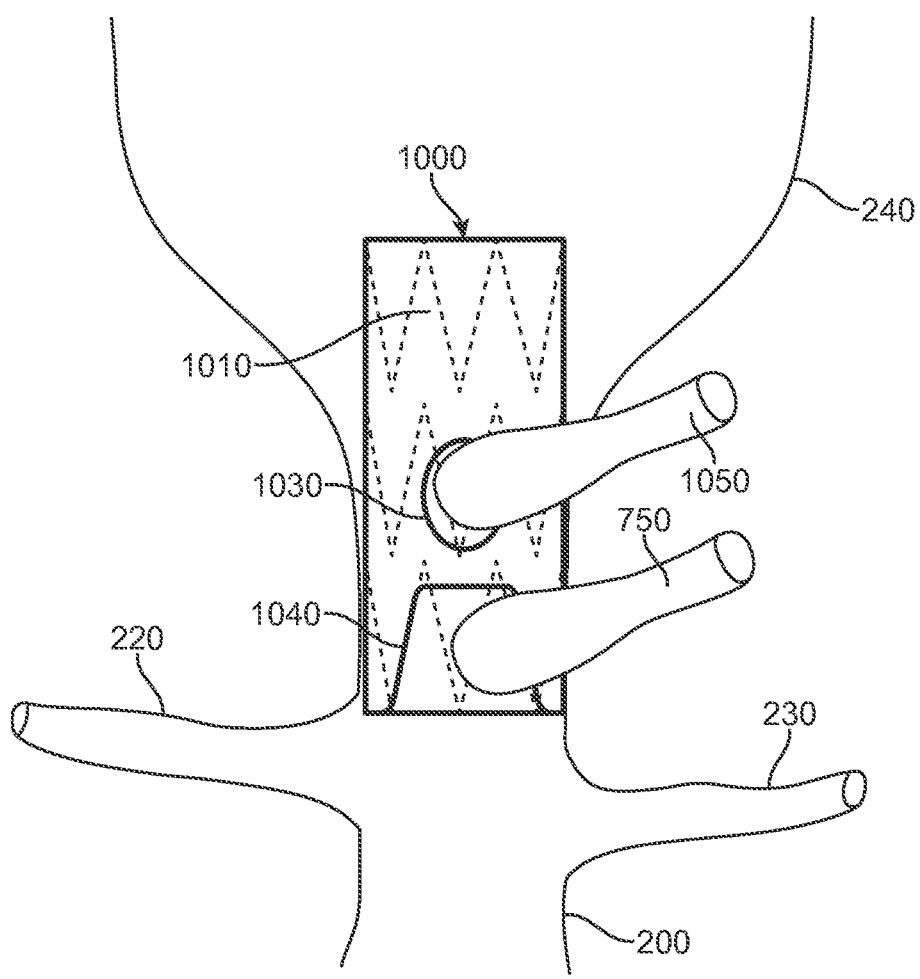

FIG. 10A-10C depict example fenestrated cuff 1000 positioned in the thoracic region of aorta 200 to treat a TAA. Cuff 1000 includes a generally cylindrical graft 1010, stent rings 1020, a fenestration 1030, and a scallop 1040. The fenestration 1030 and scallop 1040 are located such that when cuff 1000 is positioned within the aorta 200, the fenestration 1030 can be aligned with the orifice to the celiac trunk 1050 and the orifice of the SMA 750 is within the opening in the graft 1010 defined by the scallop 1040.

Thus, employing a fenestrated cuff 1000 in accordance with this disclosure to treat TAA, the celiac trunk 1050 may be employed as the datum for aligning and deploying the cuff 1000. Once the fenestration 1030 is aligned with the celiac trunk 1050, the orifice to the SMA 750 may be arranged within the opening defined by the scallop 1040. As the relative positioning of the celiac trunk 1050 and the SMA 750 differs from the distal and superior renal arteries, so does the relative position of fenestration 1030 and scallop 1040 of cuff 1000 differ from fenestrated cuffs employed to treat AAA. In this example, fenestration 1030 and scallop 1040 are axially offset and generally circumferentially aligned in graft 1010.

Although not shown in FIGS. 10A-10C, like in other examples in accordance with this disclosure, fenestrated cuff 1000 may be employed in combination with fixation mechanisms, including, e.g., helical fasteners to stabilize the position of the cuff (and endograft) and to facilitate sealing to aorta 200. For example, one or more helical fasteners may be implanted through cuff 1000 and into the wall of aorta around the periphery of fenestration 1030 and/or scallop 1040.

Figure 11:
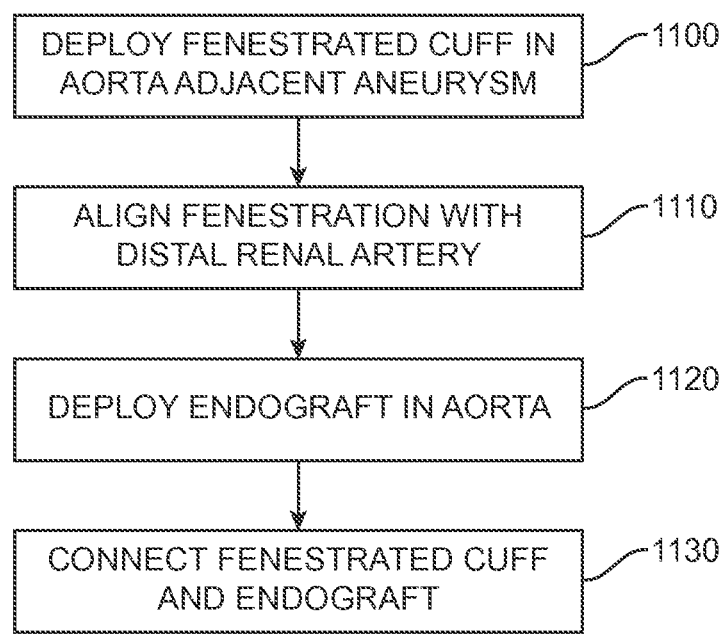
FIG. 11 is a flowchart depicting a method of implanting a fenestrated cuff in accordance with this disclosure.

FIG. 11 is a flowchart depicting an example method of implanting a fenestrated cuff. The method of FIG. 11 includes deploying a fenestrated cuff in the aorta adjacent an aneurysm (1100), aligning a fenestration of the cuff with the distal renal artery (1110), deploying a commercially available endograft into the aorta (1120), and connecting the cuff and the endograft to one another (1130).

In one example, a fenestrated cuff in accordance with this disclosure is delivered from a remote location to the aorta in the region of the aneurysm via an endovascular delivery system. For example, the cuff delivery system may include a delivery catheter in which the cuff is arranged and which includes one or more retention mechanisms for connecting the cuff to the delivery catheter and/or for retaining the cuff in a radially contracted state and/or a partially expanded state. Such deployment features of the cuff delivery system may allow the cuff to be partially deployed, recovered, and fully deployed to aid in the positioning of the cuff within the aortic lumen (or another location) and positioning the fenestration(s) at the targeted distal renal artery. In addition, the delivery system may allow the cuff to be partially or fully deployed but not released from the delivery system until the cuff is aligned, the fenestration is completed with the placement of a renal graft/stent, and/or additional fixation mechanisms, e.g., helical fasteners have been deployed.

Thus, in one example, a method of implanting a fenestrated cuff may include delivering a fenestrated cuff to a target region in the aorta adjacent an aneurysm with an endovascular cuff delivery system, at least partially deploying the cuff within the aorta, aligning a fenestration of the cuff with the distal renal artery, delivering one or more fasteners to the target region with a fastener applicator, implanting the one or more fasteners through the cuff and into the wall of the aorta to stabilize the position of the cuff, and completing deployment of the cuff and releasing the cuff from the cuff delivery system.

In addition to delivering and deploying the fenestrated cuff and fastening the cuff within the vessel using a fixation mechanism like helical fasteners, such a method can also include deploying a commercially available endograft into the aorta and connecting the cuff and the endograft to one another. Connecting the cuff and the endograft may include an additional step of delivering one or more additional fasteners using the fastener applicator a second time and then implanting the fasteners through the cuff and the endograft, and, in some cases, into the wall of the aorta.

Additional positioning of the fenestrated cuff within the aorta or another vessel may be facilitated with fasteners and fastener applicators in accordance with the disclosed examples. For example, a helical fastener can be deployed with an endovascular fastener applicator from the remote location to the aorta and positioned within the lumen of the partially deployed fenestrated cuff. The helical fastener can then be partially delivered into the graft and/or the stent of the cuff, while maintaining the connection of the helical fastener to the distal end of the fastener applicator. The distal end of the fastener applicator can then be manipulated to rotate and/or move the fenestrated cuff axially within the aorta. Additional details and examples of fastener delivery and deployment systems appropriate for such techniques of positioning example fenestrated cuffs in accordance with this disclosure are described in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY," U.S. Pat. No. 8,075,570, filed Nov. 29, 2002, and entitled "INTRALUMINAL PROSTHESIS ATTACHMENT SYSTEMS AND METHODS," and in U.S. Pat. No. 8,231,639, filed Feb. 25, 2004, and entitled "SYSTEMS AND METHODS FOR ATTACHING A PROSTHESIS WITHIN A BODY LUMEN OR HOLLOW ORGAN."

The fenestrated cuff positioned within the aorta is structured such that, once the fenestration (or other aperture in the graft of the cuff) is aligned with the distal renal artery and a fenestration graft/stent is deployed if needed, the superior rental artery (and, in some cases the SMA or other branch vessel) is positioned within the opening defined by the scallop (or other aperture) of the fenestrated cuff. After such positioning has been established, the cuff can be fully deployed (e.g., the stent structure can be fully expanded into engagement with the aorta), additional sealing and fixation mechanisms can be deployed (e.g., helical fasteners and/or an expandable cavity), and the commercially available endograft can be deployed for connection with the cuff and for completing exclusion of systematic blood flow.

Sealing and fixation can occur prior to, after, and both prior to and after the endograft is deployed and connected to the cuff. In examples in which separately delivered and deployed fasteners, e.g., helical fasteners are employed, such fasteners can be delivered via an endovascular fastener applicator as described above and in U.S. application Ser. No. 12/942,232, filed on Nov. 9, 2010, entitled "DEVICES, SYSTEMS, AND METHODS FOR PROSTHESIS DELIVERY AND IMPLANTATION, INCLUDING A PROSTHESIS ASSEMBLY," U.S. Pat. No. 8,075,570, filed Nov. 29, 2002, and entitled "INTRALUMINAL PROSTHESIS ATTACHMENT SYSTEMS AND METHODS," and in U.S. Pat. No. 8,231,639, filed Feb. 25, 2004, and entitled "SYSTEMS AND METHODS FOR ATTACHING A PROSTHESIS WITHIN A BODY LUMEN OR HOLLOW ORGAN."

In one example, from the remote location and under image guidance, a guide wire is advanced using a conventional intravascular approach into, e.g., the contralateral iliac artery and to the descending aorta. However, other access sites and methods can be utilized. The guide wire desirably extends through the lumen of the fenestrated cuff. Next, a steerable guide device is navigated over the guide wire to the desired location with respect to the fenestrated cuff. Once the steerable guide device is in position, obturator and guide wire can be removed from the body.

The steerable guide can be deflectable away from and generally perpendicular to the long axis of the guide. For example, the distal end of the steerable guide can be deflected at approximately 90 degrees relative to the axis of the guide. In practice, still employing fluoroscopy visualization, the clinician actuates deflection of the steerable guide via a handle and actuation mechanism at the proximal end of the guide catheter. The physician can then rotate the handle to rotate the flexible guide tube if necessary to orient and position the distal end of the guide for introduction of a fastener at a target location.

A fastener applicator including shaft and driver is then inserted through the lumen of the steerable guide device, and advanced until a fastener, e.g., a helical fastener, is located for deployment in relation to the now-oriented distal end of the guide. The steerable guide and fastener applicator are configured to act in concert to generate the necessary implantation force and to resolve this force to enable penetration of the cuff (and endograft) and tissue and implantation of the helical fastener.

For example, as the fastener applicator is advanced out of the distal end of the steerable guide, contacts and is pushed against the wall of the cuff and aorta, an equal and opposite resultant force pushes back on the fastener applicator and guide. The resultant force causes the steerable guide to deflect and retract relative to the fastener applicator until the guide contacts the opposite wall of the cuff and aorta. In this way, the force applied to the cuff and vascular wall from the distal end of the fastener applicator is partially or completely resolved when the steerable guide deflects and abuts the opposite wall of the cuff and aorta.

The fastener applicator can then be actuated to apply a fastener through the cuff (and endograft) and into the surrounding tissue. If the fastener applicator is a single fire device, i.e., it carries only one fastener at-a-time, the fastener applicator may be withdrawn through the lumen of the guide and a new fastener can be loaded into the distal end of the applicator. The steerable guide may then be reoriented for an additional fastening site, the fastener applicator inserted back through the lumen of the guide to apply an additional fastener to the new site. This sequence can be repeated until a desired number and array of fasteners are applied to the cuff (and endograft in some locations) and the wall of the aorta.

In some cases, the fenestrated cuff delivery system is configured to at least partially retain the cuff even through portions or all of the forgoing fastener delivery and deployment process. For example, while one or more of the helical fasteners are delivered and implanted by a guide and applicator, the proximal, distal, or proximal and distal ends of the cuff may be held and controlled, respectively, by a retaining means of the cuff delivery system.

In instances in which a fenestration graft is employed, the fenestration graft can also be delivered by an endovascular delivery system. The delivery system employed to deliver the fenestration graft may be the same or different from the system employed to deliver the cuff and/or the endograft. In one example, the fenestration graft is delivered, deployed, and connected to the fenestration of the cuff after the fenestration has been aligned with the distal renal artery under fluoroscopy.

Figure 12A:
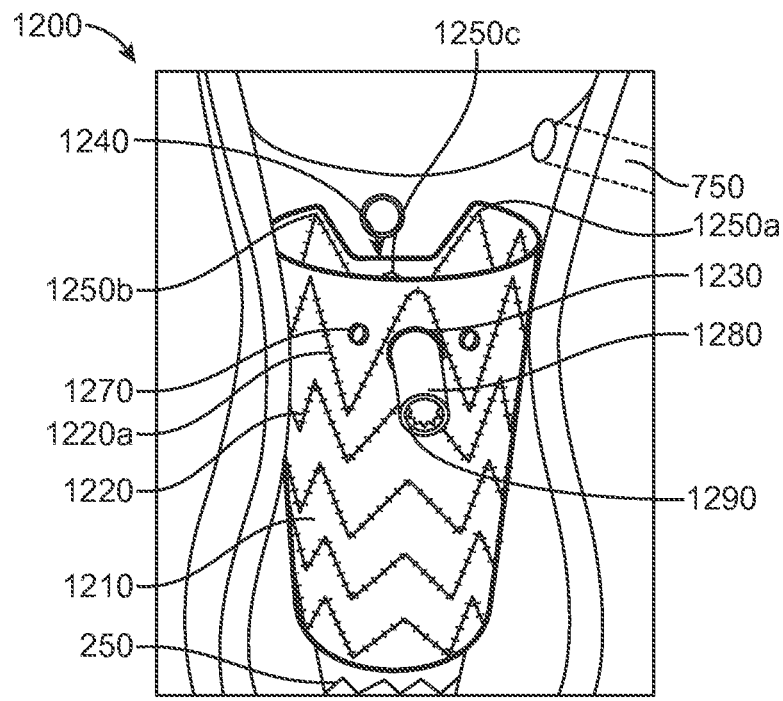
FIGS. 12A and 12B are perspective views depicting another example fenestrated cuff in accordance with this disclosure.
Figure 12B:
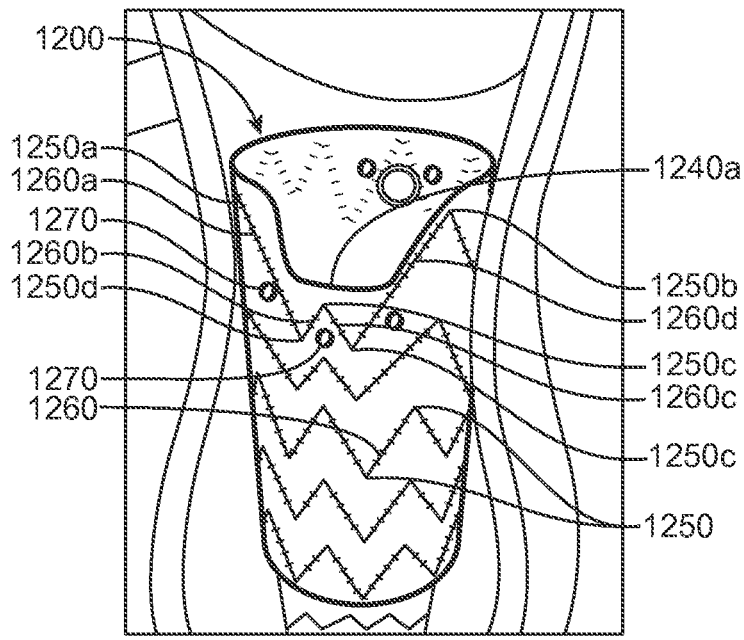

FIGS. 12A and 12B depict another example fenestrated cuff 1200 including a generally cylindrical graft 1210, stent rings 1220, a fenestration 1230, and a scallop 1240. The example of FIGS. 12A and 12B also includes a fenestration graft 1280 extending from fenestration 1230 into the distal renal artery and including stent 1290. Fenestrated cuff 1200 may be similar in size, shape, components, and/or function as fenestrated cuff 100. However, in this example, the proximal stent ring 1220a does not extend across the opening defined by the scallop 1240. Instead, the proximal stent ring 1220a is sized and shaped to extend circumferentially around the opening defined by the scallop 1240. As illustrated in FIG. 12B, for example, the apices and stent segments of stent ring 1220a are arranged and sized such that the proximal stent ring 1220a surrounds the periphery of scallop 1240.

In the example of cuff 1200, proximal apices 1250a and 1250b are arranged on either side of the scallop 1240 adjacent the proximal end of graft 1210. Proximal apex 1250c is arranged below and adjacent the circumferentially extending edge 1240a of scallop 1240. Finally, proximal apices 1250a, 1250b, 1250c, and adjacent distal apices 1250d and 1250e are connected by different length stent segments 1260a-1260d. In the example of cuff 1200, stent segments 1260b and 1260c are shorter than stent segments 1260a and 1260d. Excluding stent struts and apices from the opening defined by the scallop 1240 (or other apertures in example fenestrated cuffs in accordance with this disclosure) may function to reduce the potential for renal emboli and/or vessel trauma and may leave open the option of additional endovascular repairs and/or renal fenestrations in a future operation/secondary intervention.

Fenestrated cuff 1200 also includes fenestration graft 1280 connected to and extending into the distal renal artery. This example illustrates that fenestration grafts employed in examples according to this disclosure may include a stent, e.g., fenestration graft stent 1290 connected to fenestration graft 1280. Fixation and sealing of fenestrated cuff 1200 is facilitated and improved by employing a plurality of helical fasteners 1270. In this example, helical fasteners 1270 are arranged and implanted around fenestration 1230 and a portion of scallop 1240.

The devices, systems, and methods in accordance with this disclosure can be employed for treating aortic dissections and aneurysms of the aorta, including those that occur in the thoracic region between the aortic arch and renal arteries, as well as aneurysms that occur in the abdominal region, usually in the infrarenal area between the renal arteries and the aortic bifurcation. Some of the conditions for which examples according to this disclosure can be used are described below with reference to FIGS. 13-15B. However, the disclosed devices, systems, and methods are applicable for use in treating other dysfunctions elsewhere in the body, which are not necessarily aorta-related or specifically described below and illustrated in the associated figures.

Figures 13, 14A:
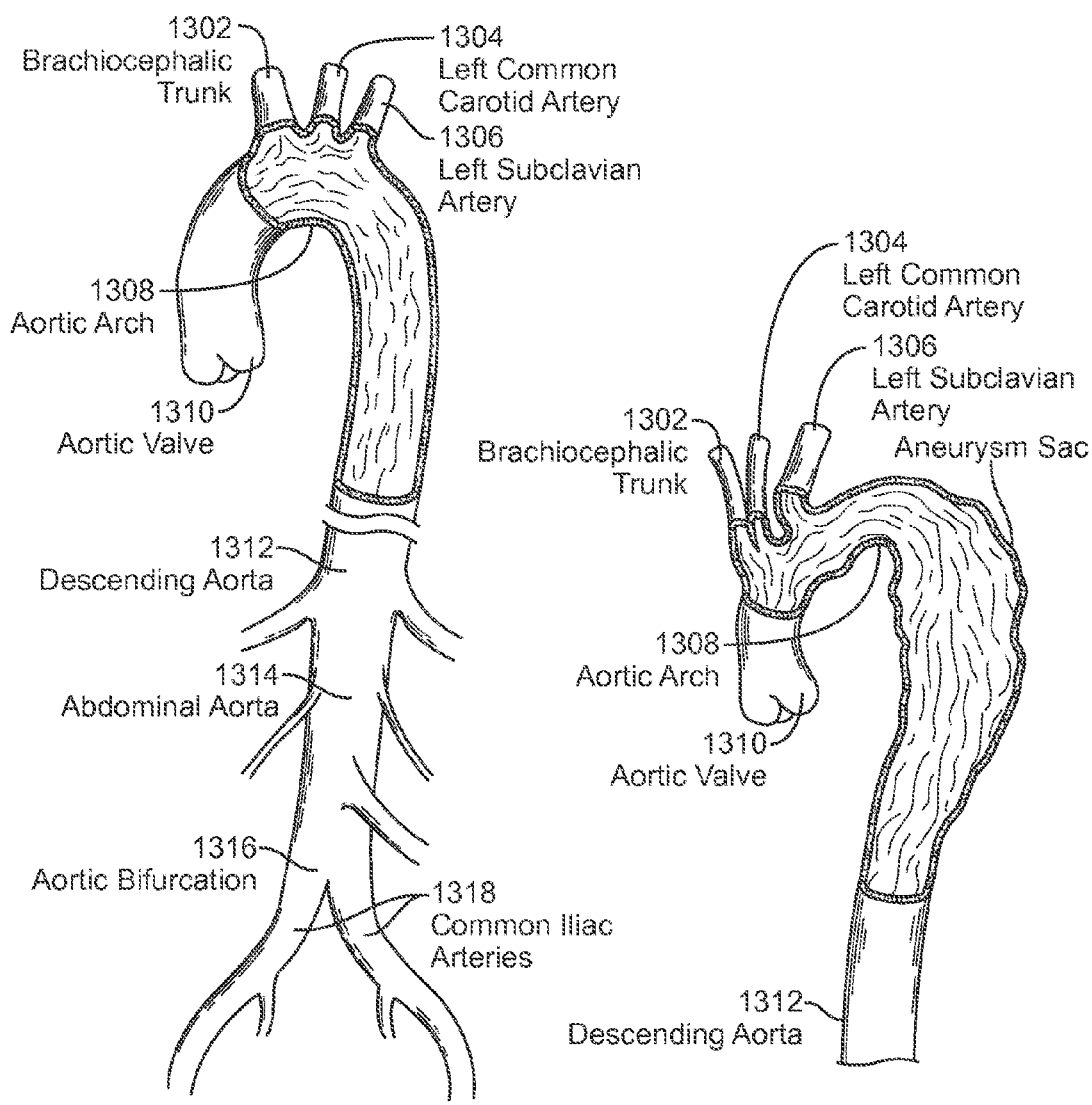
FIG. 13 is a perspective view of a healthy aorta showing the extent of the aorta from the aortic root, through the aortic arch, the descending thoracic aorta, and to the abdominal aorta and aortic bifurcation.
FIGS. 14A, 14B, and 14C are perspective views of diseased aortas, showing the extent to which aneurysms may deform the aorta.

A healthy aorta, the body's largest artery, has a general shape like the handle portion of a walking cane (see FIG. 13). FIG. 13 illustrates the brachiocephalic trunk 1302, the left common carotid artery 1304, the left subclavian artery 1306, the aortic arch 1308, the aortic valve 1310, the descending aorta 1312, the abdominal aorta 1314, the aortic bifurcation 1316, and the common iliac arteries 1318. The short length of the curved handle comes out of the heart and curls through the aortic arch 1308. Multiple smaller arteries 1302, 1304, 1306 branch off at the aortic arch 1308 to serve the head and arms. The aorta continues to descend through the chest cavity into the abdomen and separates to provide blood to the abdominal organs and both legs. Various abnormalities may affect the aorta, most of which are considered potentially life-threatening. Prevalent aortic abnormalities include aortic aneurysms and aortic dissections, as non-limiting examples.

Figure 14B:
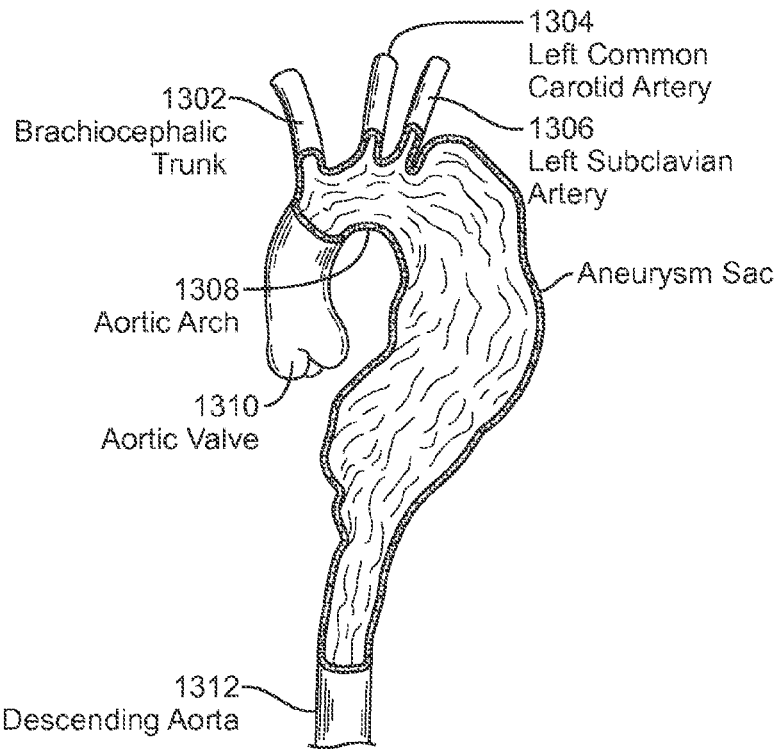
Figure 14C:
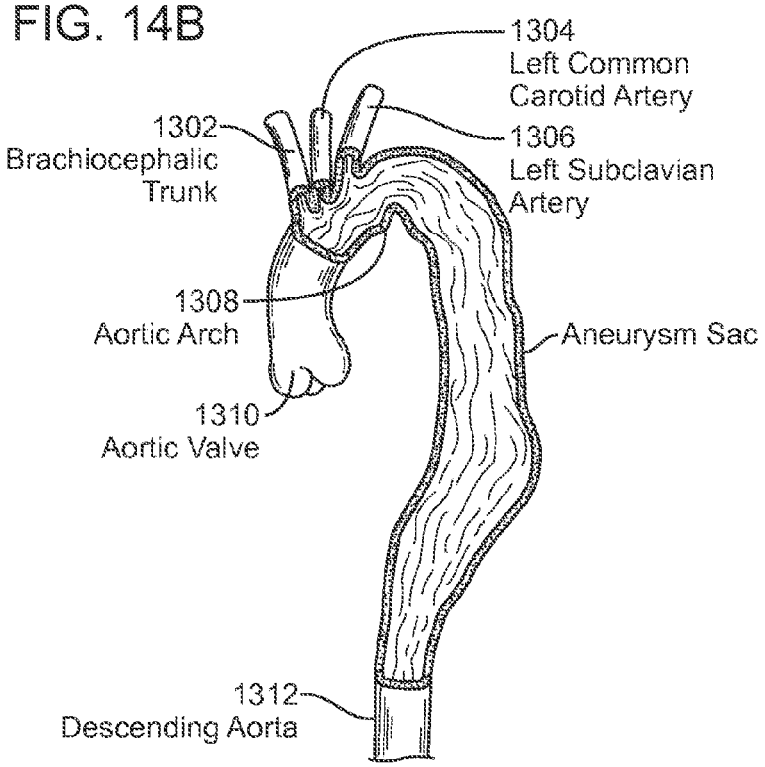

Aneurysms may affect one or more segments of the thoracic aorta, including the ascending aorta, the arch 1308, and the descending thoracic aorta. A thoracic aortic aneurysm (TAA) can be described as an expanded (bulging) section(s) of the wall of the aorta, and is considered a life-threatening condition. Thoracic aortic aneurysms of any size can cause significant short- and long-term mortality due to rupture and dissection. FIGS. 14A to 14C show examples of aortas having diseased tissues and difficult cases where the left subclavian artery ostium is distal to the aortic arch. Relative positions of the aneurysmal tissues in the tortuous aortic arch can be seen, as can and relationship to the brachiocephalic trunk 1302, left common carotid artery 1304, and the left subclavian artery 1306. Often the left subclavian artery 1306 provides a landmark for positioning of an endovascular graft (to be described in greater detail below).

Common causes of a thoracic aortic aneurysm include hardening of the arteries (atherosclerosis), degeneration of the media of the aortic wall, as well as from local hemodynamic forces. Additional risk factors include various connective tissue disorders such as Marfan syndrome, previous dissection of the aorta, and trauma such as falls or motor vehicle accidents. They also sometimes occur in people who have bicuspid aortic valves.

Figure 15A:
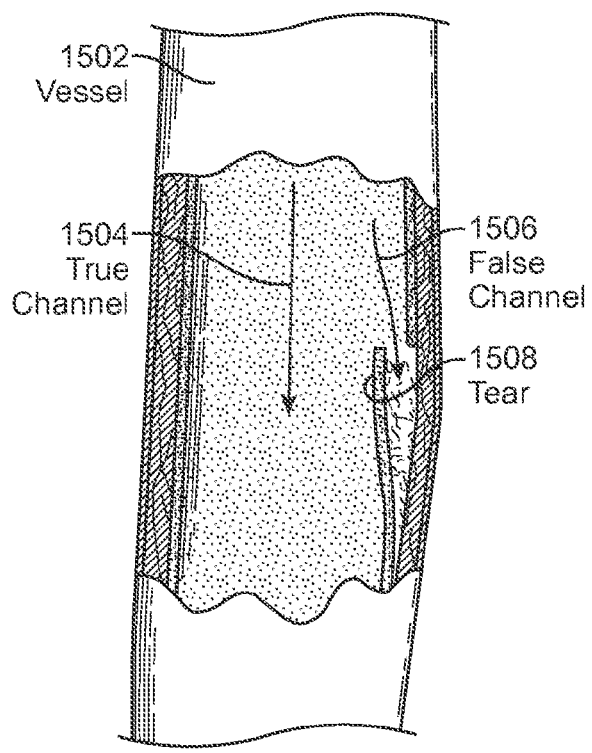
FIGS. 15A and 15B are perspective views of diseased aortas, showing aortic dissections.
Figure 15B:
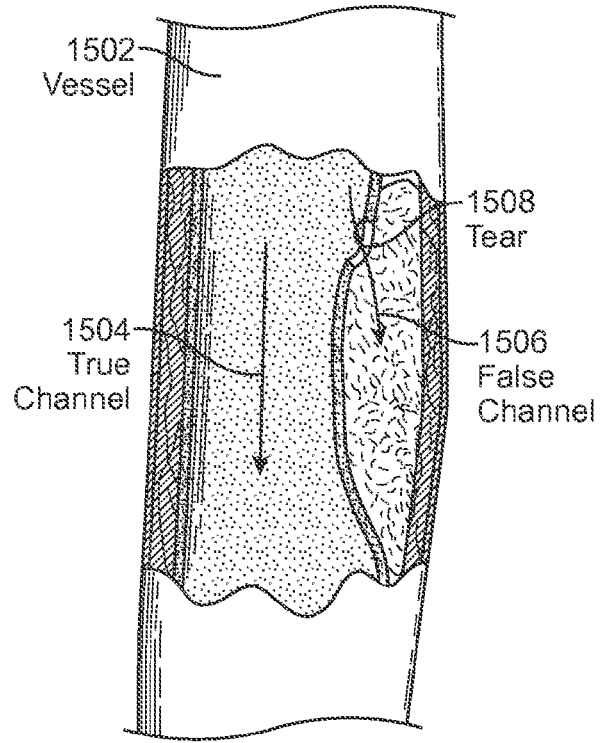

An aortic dissection is a perforation or tear in the lining of the aorta. The tear allows blood to flow between the layers of the aortic wall, with the force of the blood forcing the layers of the wall apart. FIGS. 15A and 15B show views of aortic dissections including a vessel 1502, a true channel 1504, a false channel 1506, and a tear 1508. An aortic dissection is a medical emergency and can quickly lead to death. If the dissection tears the aortic wall completely open, massive and rapid blood loss occurs.

The tearing of the inner lining of the aorta causes the blood to separate along the wall of the artery. This generally causes two channels in the vessel, with one channel referred to as the true channel 1504 and the other channel referred to as the false channel 1506. As can be seen in FIGS. 15A and 15B, the tear 1508 allows the blood to create the false channel 1506. With each heartbeat, the artery may progressively tear more and more with blood propagating down the false channel 1506 blocking off the true channel 1504 and the flow of blood to some or all of the branches of the aorta.

Aortic dissections can be classified by the Stanford method into a type A or type B depending on the location and the extent of the dissection. Type A dissection, or proximal dissection, involves the ascending aorta and aortic arch, and may or may not involve the descending aorta. Type B dissection, or distal dissection, usually begins just distal to the ostium of the left subclavian artery, extending distally into the descending and abdominal aorta. If left untreated, the risk of death from aortic dissection can reach 30 percent within fifteen minutes after onset of symptoms and 75 percent by one week.

Figure 16:
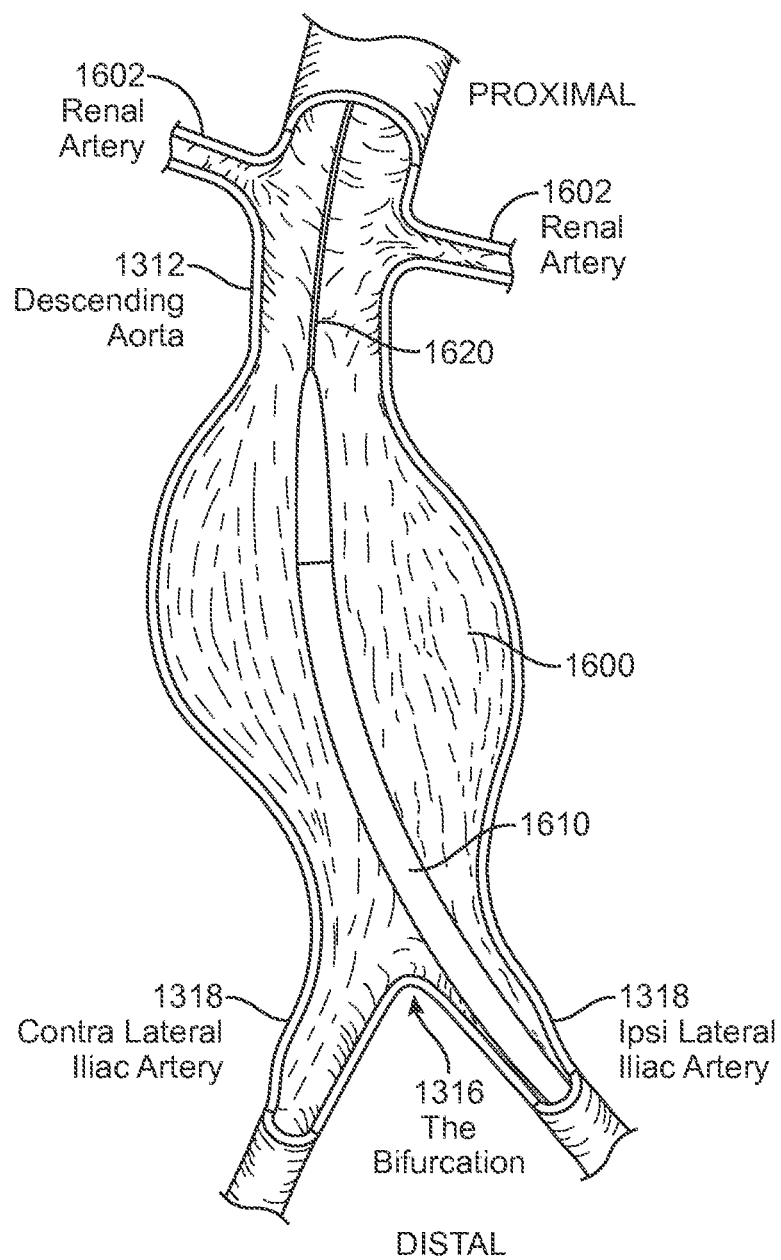
FIG. 16 depicts an example of the abdominal aorta with an aneurysm in the infrarenal area between the renal arteries and the aortic bifurcation.

FIG. 16 depicts an example of the abdominal aorta with an aneurysm 1600 in the infrarenal area between the renal arteries and the aortic bifurcation. In this example, an endovascular delivery device 1610 is delivered to the region via guidewire 1620 and is in the process of being positioned for deploying a prosthesis within the aorta. The device 1610 may be used, for example, to deliver and deploy a fenestrated cuff in accordance with this disclosure. In such cases, the delivery device 1610 may include one or more retention and release mechanisms, which may facilitate, among other functions, aligning and deploying the cuff, as described above.

When referring to different structures in the examples according to this disclosure, including, e.g., an endovascular prostheses and/or its components and/or portions of a fastener and/or prosthesis delivery system and/or fastener delivery system, the terms "proximal," "distal," "anterior," "posterior," "medial," and "lateral" may be used to describe the relation or orientation of such structures with respect to a patient's heart after implantation. The term "proximal" will be used to describe a relation or orientation of a structure that, when implanted and/or otherwise in situ, is toward the heart, and the term "distal" will be used to describe a position or orientation of the structure that, when implanted and/or otherwise in situ, is away from the heart, i.e., toward the feet. "Anterior" refers to a relation or orientation of a structure that, when implanted and/or otherwise in situ, is generally toward the front of a patient, and "posterior" refers to the opposite of anterior, i.e., toward the back of the patient. "Medial" refers to a relation or orientation of a structure that, when implanted and/or otherwise in situ, is closer to the midline of the body of a patient, and "lateral" refers to the opposite of medial, i.e., farther away from the midline.

When referring to implantation apparatus or devices that are manipulated by a physician or operator, the terms "proximal" and "distal" will be used to describe the relation or orientation of the apparatus or device with respect to the operator as it is used. Therefore, the term "proximal" will be used to describe a relation or orientation of the apparatus or device that, when in use, is positioned toward the operator (i.e., at the handle end of the device), and the term "distal" will be used to describe a position or orientation of the apparatus or device that, when in use, is positioned away from the operator (i.e., at the other end of a catheter or the like away from the handle).

Various examples have been described. These and other examples are within the scope of the following claims.

What is claimed is:

1. A system for treating an aneurysm in the aorta, the system comprising:
   a fenestrated cuff comprising:
      a cylindrical graft comprising first and second apertures, the first aperture being arranged generally opposite the second aperture in the graft, the first and second apertures being sized and shaped such that, when one of the first and second apertures is aligned with the distal renal artery, an orifice of the superior renal artery is within the other of the first and second apertures, wherein the first aperture comprises a fenestration and the second aperture comprises a scallop; and
      at least one stent ring configured to expand into engagement with an inner wall of the aorta, wherein the scallop is arranged at and defines an opening in one of first and second ends of the graft, and the at least one stent ring comprises a proximal stent ring arranged adjacent the one of the first and second ends of the graft extending circumferentially around and not into the opening defined by the scallop, the proximal stent ring surrounding a periphery of the scallop; and
   a plurality of fasteners, at least one of the fasteners for deployment through the fenestrated cuff and into a wall of the aorta above the distal renal artery, and at least one other of the fasteners for deployment through the fenestrated cuff and into the wall of the aorta between the distal renal artery and a sac of the aneurysm.

2. The system of claim 1, wherein at least one of the fasteners comprises a helical fastener comprising a sharp distal tip and cross-bar at the proximal end of the fastener.

3. The system of claim 1, wherein the fenestrated cuff comprises a fenestration graft connected to and extending radially outward from the fenestration.

4. The system of claim 1, wherein the proximal stent ring arranged adjacent the one of the first and second ends of the graft and extending circumferentially around the opening defined by the scallop is connected to the graft adjacent the scallop.

5. The system of claim 1, wherein lengths of two or more of linear stent segments of at least one of the plurality of stent rings are different.

\* \* \* \* \*